(12) United States Patent
Abouabdellah et al.

(10) Patent No.: US 7,439,257 B2
(45) Date of Patent: Oct. 21, 2008

(54) ARYLOXYALKYLCARBAMATE-TYPE DERIVATIVES, PREPARATION METHOD THEREOF AND USE OF SAME IN THERAPEUTICS

(75) Inventors: Ahmed Abouabdellah, Thiais (FR); Antonio Almario Garcia, Chatenay Malabry (FR); Jacques Froissant, Brevainville (FR); Christian Hoornaert, Antony (FR)

(73) Assignee: Sanofi-Aventis, Paris (FR)

( * ) Notice: Subject to any disclaimer, the term of this patent is extended or adjusted under 35 U.S.C. 154(b) by 142 days.

(21) Appl. No.: 11/456,708

(22) Filed: Jul. 11, 2006

(65) Prior Publication Data
US 2007/0021424 A1    Jan. 25, 2007

Related U.S. Application Data

(63) Continuation of application No. PCT/FR2005/000028, filed on Jan. 7, 2005.

(30) Foreign Application Priority Data
Jan. 16, 2004    (FR) ................... 04 00389

(51) Int. Cl.
*A61K 31/445* (2006.01)
*C07D 211/06* (2006.01)

(52) U.S. Cl. .................. 514/330; 546/227; 546/216; 546/152; 546/139; 548/531; 560/157; 514/307; 514/314; 514/327; 514/423; 514/478

(58) Field of Classification Search ............. 514/330, 514/307, 314, 327, 423, 478; 546/227, 216, 546/152, 139; 548/531; 560/157
See application file for complete search history.

(56) References Cited

U.S. PATENT DOCUMENTS

| 6,096,773 | A | 8/2000 | Scott et al. | |
| 6,194,448 | B1 | 2/2001 | Biediger et al. | |
| 7,119,116 | B2 * | 10/2006 | Abouabdellah et al. | 514/452 |

FOREIGN PATENT DOCUMENTS

| WO | WO 02/087569 | 11/2002 |
| WO | WO 03/065989 | 8/2003 |
| WO | WO 2004/067498 | 8/2004 |

OTHER PUBLICATIONS

Tarzia, G., et. al., Design, Synthesis, and Structure-Activity Relationships of Alkylcarbamic Acid Aryl Esters, a New Class of Fatty Acid Amide Hydrolase Inhibitors, J. Med. Chem. 2003 vol. 46, pp. 2352-2360.

* cited by examiner

*Primary Examiner*—Charanjit S Aulakh
(74) *Attorney, Agent, or Firm*—Balaram Gupta

(57) ABSTRACT

The invention relates to a compound of formula (I):

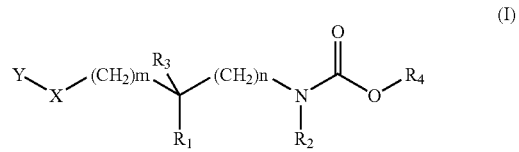

Wherein m, n, X, Y, $R_1$, $R_2$, $R_3$ and $R_4$ are as defined herein. The invention also relates to the use of same in therapeutics.

9 Claims, No Drawings

ARYLOXYALKYLCARBAMATE-TYPE DERIVATIVES, PREPARATION METHOD THEREOF AND USE OF SAME IN THERAPEUTICS

CROSS REFERENCE TO RELATED APPLICATIONS

This application is a continuation of International application No. PCT/FR2005/000,028, Jan. 7, 2005, which is incorporated herein by reference in its entirety; which claims the benefit of priority of French Patent Application No. 04/00,389, filed Jan. 16, 2004.

BACKGROUND OF THE INVENTION

FIELD OF THE INVENTION

The invention relates to aryloxyalkyl-carbamate derivatives, to their preparation and to their application in therapy.

SUMMARY OF THE INVENTION

The compounds of the invention conform to the general formula (I):

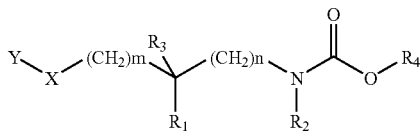

in which
  m represents 0, 1, 2 or 3;
  n represents 0, 1, 2 or 3;
  X represents an oxygen or sulfur atom or an SO or $SO_2$ group;
  $R_1$ and $R_2$ represent independently of one another a hydrogen atom or a $C_{1-3}$ alkyl group, or $R_1$ and $R_2$ together form a group $-(CH_2)_p-$, where p represents an integer ranging from 1 to 5 such that n+p is an integer ranging from 2 to 5;
  $R_3$ represents a hydrogen or fluorine atom or a hydroxyl or methyl group;
  $R_4$ represents a group of general formula $CHR_5CONHR_6$ in which
    $R_5$ represents a hydrogen atom or a $C_{1-6}$ alkyl group and
    $R_6$ represents a hydrogen atom or a $C_{1-6}$ alkyl, $C_{3-7}$ cycloalkyl or $C_{3-7}$ cycloalkyl-$C_{1-6}$ alkylene group;
  Y represents a group $Y_1$ selected from in particular a phenyl, pyridinyl, pyridazinyl, pyrimidinyl, pyrazinyl, triazinyl, thiazolyl, naphthyl, quinolinyl, isoquinolinyl, phthalazinyl, quinazolinyl, quinoxalinyl, naphthyridinyl, cinnolinyl, benzofuranyl, dihydrobenzofuranyl, benzothienyl, dihydrobenzothienyl, indolyl, isoindolyl, indolinyl, benzimidazolyl, benzoxazolyl, benzisoxazolyl, benzothiazolyl, benzisothiazolyl, benzotriazolyl, benzoxadiazolyl and benzothiadiazolyl; the group $Y_1$ being optionally substituted by one or more substituents $Y_2$, which are identical to or different from one another, or by a group $Y_3$;

$Y_2$ represents a halogen atom or a cyano, nitro, $C_{1-8}$ alkyl, $C_{1-8}$ alkoxy, $C_{1-8}$ thioalkyl, $C_{1-8}$ fluoroalkyl, $C_{1-8}$ fluoroalkoxy, $C_{1-8}$ fluorothioalkyl, $C_{3-7}$ cycloalkyl, $C_{3-7}$ cycloalkyloxy, $C_{3-7}$ cycloalkyl-$C_{1-8}$ alkylene, $C_{3-7}$ cycloalkyl-$C_{1-8}$ alkyloxy, hydroxyl, $NR_7R_8$, $NHCOR_7$, $NHSO_2R_7$, $COR_7$, $CO_2R_7$, $CONR_7R_8$, $SO_2R_7$, $SO_2NR_7R_8$, $-O-C_{1-3}$ alkylene)-O-, phenyloxy, phenylthio, phenyl-$C_1$-$C_8$ alkylene, phenyl-$C_1$-$C_8$ alkyloxy or phenyl-$C_1$-$C_8$ alkylthio group;

$Y_3$ represents a group selected from in particular a phenyl, pyridinyl, pyrimidinyl, pyrazinyl or pyridazinyl;

it being possible for the group or groups $Y_3$ to be substituted by one or more groups $Y_2$ which are identical to or different from one another;

$R_7$ and $R_8$ represent independently of one another a hydrogen atom or a $C_{1-6}$ alkyl group, or with the nitrogen atom carrying them form an azetidine, pyrrolidine, piperidine, morpholine, thiomorpholine, azepine or piperazine ring optionally substituted by a $C_{1-3}$ alkyl or benzyl group.

DETAILED DESCRIPTION OF THE INVENTION

Among the compounds of general formula (I) a first group of compounds is that for which:
  Y represents a group $Y_1$ selected from in particular a phenyl, pyridinyl, pyrimidinyl, thiazolyl, naphthyl, quinolinyl, isoquinolinyl and benzoxazolyl; the group $Y_1$ being optionally substituted by one or more substituents, more particularly by one or two substituents, $Y_2$, which are identical to or different from one another, or by a group $Y_3$;

$Y_2$ represents a halogen atom, more particularly a chlorine, a fluorine or a bromine, a cyano, $C_{1-8}$ alkyl, more particularly a methyl, isopropyl, butyl, tert-butyl or tetramethylbutyl, $C_{1-8}$ alkoxy, more particularly a methoxy, ethoxy or propoxy, $C_{1-8}$ fluoroalkyl, more particularly a trifluoromethyl, $C_{1-8}$ fluoroalkoxy, more particularly a trifluoromethoxy, phenyloxy or phenyl-$C_1$-$C_8$ alkylene group, more particularly a phenyl(1,1-dimethylmethylene);

$Y_3$ represents a phenyl group; it being possible for $Y_3$ to be substituted by one or more groups, more particularly by one or two groups, $Y_2$ which are identical to or different from one another.

Among the compounds of the first group as defined above a second group of compounds is that for which:
  Y represents a group $Y_1$ selected from in particular a phenyl or a naphthyl; the group $Y_1$ being optionally substituted by one or more substituents, more particularly by one or two substituents, $Y_2$, which are identical to or different from one another, or by a group $Y_3$;

$Y_2$ represents a halogen atom, more particularly a chlorine, a fluorine or a bromine, a cyano, $C_{1-8}$ alkyl, more particularly a methyl, isopropyl, butyl, tert-butyl or tetramethylbutyl, $C_{1-8}$ alkoxy, more particularly a methoxy, ethoxy or propoxy, $C_{1-8}$ fluoroalkyl, more particularly a trifluoromethyl, $C_{1-8}$ fluoroalkoxy, more particularly a trifluoromethoxy, phenyloxy or phenyl-$C_1$-$C_8$ alkylene group, more particularly a phenyl(1,1-dimethylmethylene);

$Y_3$ represents a phenyl group; it being possible for $Y_3$ to be substituted by one or more groups, more particularly by one or two groups, $Y_2$ which are identical to or different from one another.

Among the compounds of general formula (I) a third group of compounds is that for which:
  m represents 0, 1, 2 or 3; and/or
  n represents 0, 1, 2 or 3; and/or
  $R_1$ and $R_2$ represent independently of one another a hydrogen atom or a $C_{1-3}$ alkyl group, or $R_1$ and $R_2$ together form a group —$(CH_2)_p$—, where p represents an integer ranging from 1 to 5 such that n+p is an integer ranging from 2 to 5;

with the proviso that, when $R_1$ and $R_2$ represent independently of one another a hydrogen atom or a $C_{1-3}$ alkyl group, m+n>1.

Among the compounds of the third group as defined above, a fourth group of compounds is that for which:
m represents 0, 1, 2 or 3; and/or
n represents 0, 1, 2 or 3; and/or
$R_1$ and $R_2$ together form a group —$(CH_2)_p$—, where p represents an integer ranging from 1 to 4 such that n+p is equal to 4.

Among the compounds of general formula (I), a fifth group of compounds is that for which X represents an oxygen atom.

Among the compounds of general formula (I), a sixth group of compounds is that for which $R_3$ represents a hydrogen atom.

A seventh group is formed of the compounds for which simultaneously $R_1, R_2, R_3, R_4, R_5, R_6, R_7, R_8, X, Y, Y_1, Y_2, Y_3$, n and m are as defined in the subgroups of compounds above.

The compounds of general formula (I) may include one or more asymmetric carbons. They may exist in the form of enantiomers or diastereoisomers. These enantiomers and diastereoisomers, and also mixtures thereof, including the racemic mixtures, form part of the invention.

The compounds of formula (I) may exist in the form of bases or of addition salts with acids. Such addition salts form part of the invention.

These salts are advantageously prepared with pharmaceutically acceptable acids, although the salts of other acids which are of use, for example, for purifying or isolating compounds of formula (I) likewise form part of the invention. The compounds of general formula (I) may be in the form of hydrates or solvates, namely in the form of associations or combinations with one or more molecules of water or with a solvent. Such hydrates and solvates likewise form part of the invention.

In the context of the invention the terms are understood as follows:
$C_{t-z}$, where t and z may take the values from 1 to 8, is a carbon chain which may have from t to z carbon atoms; for example, $C_{1-3}$ is a carbon chain which may have from 1 to 3 carbon atoms;
alkyl is a saturated, linear or branched aliphatic group; for example, a $C_{1-3}$ alkyl group represents a linear or branched carbon chain of 1 to 3 carbon atoms, more particularly a methyl, ethyl, propyl or 1-methylethyl;
alkylene is a saturated, linear or branched divalent alkyl group; for example, a $C_{1-3}$ alkylene group represents a linear or branched, divalent carbon chain of 1 to 3 carbon atoms, more particularly a methylene, ethylene, 1-methylethylene, propylene or 1,1-dimethyl-methylene;
cycloalkyl is a cyclic alkyl group; for example, a $C_{3-5}$ cycloalkyl group represents a cyclic carbon group of 3 to 5 carbon atoms, more particularly a cyclopropyl, cyclobutyl or cyclopentyl;
alkenylene is a divalent unsaturated aliphatic group containing at least 2 carbons, more particularly an ethylene;
alkoxy is an —O-alkyl group having a saturated, linear or branched aliphatic chain;
thioalkyl is an —S-alkyl group having a saturated linear or branched aliphatic chain;
fluoroalkyl is an alkyl group in which one or more hydrogen atoms have been substituted by a fluorine atom;

fluoroalkoxy is an alkoxy group in which one or more hydrogen atoms have been substituted by a fluorine atom;
fluorothioalkyl is a thioalkyl group in which one or more hydrogen atoms have been substituted by a fluorine atom; and
a halogen atom is a fluorine, a chlorine, a bromine or an iodine.

The compounds of the invention may be prepared according to different methods, which are illustrated by the schemes which follow.

Thus one method of preparation (Scheme 1) consists in reacting an amine of general formula (II), in which Y, X, $R_1$, $R_2$, $R_3$, m and n are as defined in the general formula (I), with a carbonate of general formula (III), in which Z represents a hydrogen atom or a nitro group, $R_5$ is as defined in the general formula (I) and R represents a methyl or ethyl group, in a solvent such as toluene or dichloroethane, at a temperature of between 0 and 80° C. The resultant carbamate esters of general formula (IV) are subsequently converted into compounds of general formula (I) by aminolysis, by means of an amine of general formula $R_6NH_2$ where $R_6$ is as defined in the general formula (I). The aminolysis reaction may be carried out in a solvent such as methanol or ethanol, or a mixture of solvents such as methanol and tetrahydrofuran.

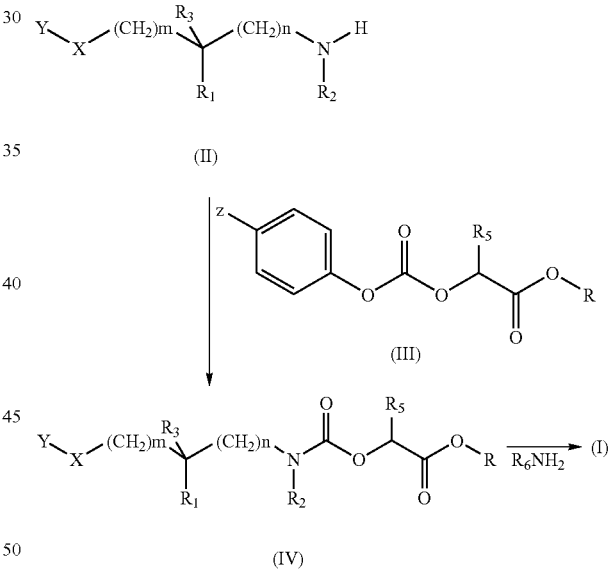

Another method (Scheme 2) of obtaining the compounds of general formula (I) in which $R_2$ represents more particularly a hydrogen atom consists in reacting a derivative of general formula (IIa) in which W represents a hydroxyl, mesylate or tosylate group or a chlorine, bromine or iodine atom, and in which Y, X, $R_1$, $R_3$, m and n are as defined in the general formula (I), with an oxazolidine dione of general structure (V), in which $R_5$ is as defined in the general formula (I), to give the oxazolidine dione derivative of general structure (VI). In the case where W represents a hydroxyl group the reaction may be conducted according to the conditions of Mitsunobu (Synthesis, 1981, 1-28); for example, by the action of diethyl or diisopropyl azodicarboxylate in the presence of triphenylphosphine. In the case where W represents a chlorine, bromine or iodine atom or a mesylate or tosylate group the reaction may be conducted in the presence of a base such as 1,1,3,3-tetramethylguanidine, sodium hydride or sodium tert-butoxide in a solvent such as tetrahydrofuran, acetonitrile or dimethylformamide at a temperature of between 0° C. and the reflux temperature of the solvent. The resultant oxazolidine dione derivative of general formula (VI) is subsequently converted into a compound of general formula (I) by aminolysis, by means of an amine of general formula $R_6NH_2$ where $R_6$ is as defined in the general formula (I).

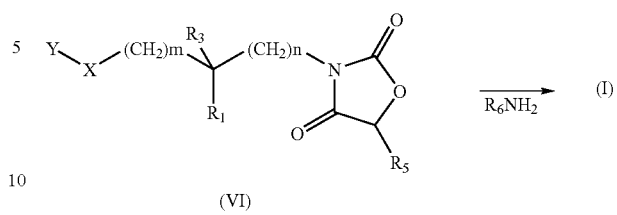

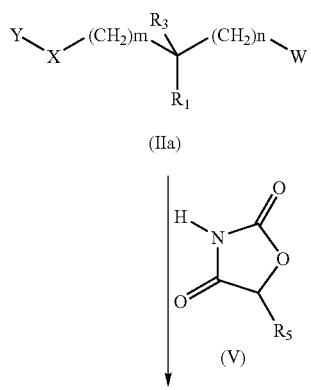

Another variant (Scheme 3), for obtaining the compounds of general formula (I) in which X represents more particularly an oxygen atom, consists in reacting an alcohol derivative of general formula (VIIa), (VIIb) or (VIIc) with a phenol derivative of general structure YOH, in which the Y is as defined in the general formula (I), for example in accordance with the Mitsunobu reaction conditions (Synthesis, 1981, 1-28) or modified conditions (Tetrahedron Letters 1993, 34, 1639-1642), the carbamate ester (IVa) and oxazolidine dione (VIa) derivatives being subsequently converted into compounds of general formula (I) by aminolysis reaction by means of an amine of general structure $R_6NH_2$ where $R_6$ is as defined in the general formula (I).

In the general formulae (VIIa), (VIIb) and (VIIc), the groups $R_1$, $R_2$, $R_3$, $R_5$, $R_6$, m, n and R are as defined above.

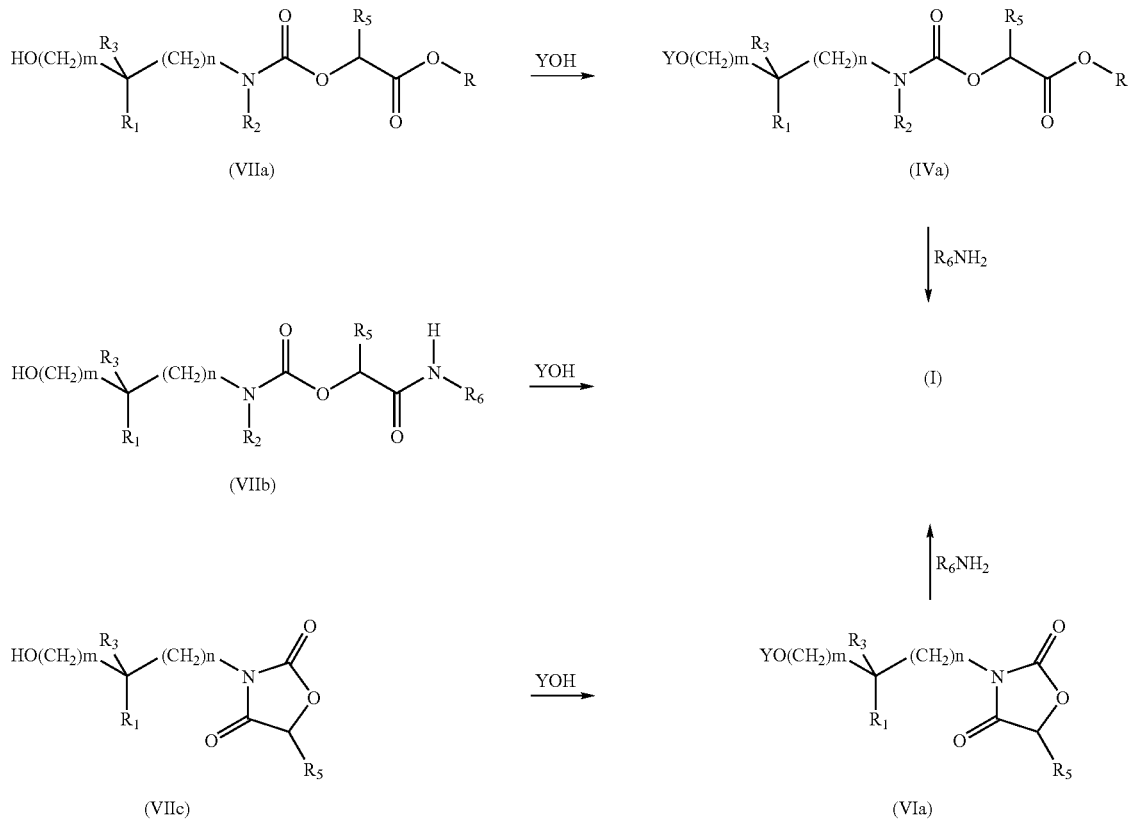

Another variant (Scheme 4) for obtaining the compounds of general formula (I) in which Y represents more particularly a group $Y_1$-$Y_3$ of aryl-aryl, aryl-heteroaryl, heteroaryl-aryl or heteroaryl-heteroaryl type, consists in reacting an aryl halide derivative of general structure (VIII), in which U is a bromine or iodine atom and $Y_1$, X, $R_1$, $R_2$, $R_3$, $R_5$, $R_6$, n and m are as defined in the general formula (I), with an arylboronic or heteroarylboronic acid derivative of formula $Y_3B(OH)_2$, where $Y_3$ is as defined in the general formula (I), in accordance with the Suzuki reaction conditions (Chem. Rev. 1995, 95, 2457-2483) or with an aryl- or heteroaryl-tri-alkylstannane derivative of formula $Y_3Sn(R')_3$, where $Y_3$ is as defined in the general formula (I) and R' is a $C_{1-4}$ alkyl, in accordance with the Stille reaction conditions (Angew. Chem. Int. Ed. 1986, 25, 504-524).

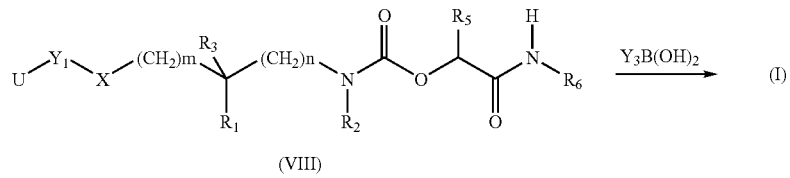

The compounds of general formulae (II), (IIa), (III), (V), (VIIa), (VIIb), (VIIc) and (VIII) and the phenol derivatives of general structure YOH, when the method by which they are prepared is not described, are available commercially or are described in the literature, or else may be prepared according to methods which are described therein or which are known to the person skilled in the art.

The amines of general formula $R_6NH_2$ are available commercially.

The examples which follow illustrate the preparation of some compounds of the invention. These examples are not limitative, and merely illustrate the invention. The microanalyses, the IR and NMR spectra and/or the LC-MS (Liquid Chromatography coupled to Mass Spectroscopy) confirm the structures and purities of the compounds obtained.

m.p. (° C.) represents the melting point in degrees Celsius.

The numbers indicated in parentheses in the titles of the examples correspond to those from the 1st column of the table thereafter.

The IUPAC (International Union of Pure and Applied Chemistry) nomenclature has been used for naming the compounds in the following examples. For example, for the biphenyl group, the following numbering has been respected:

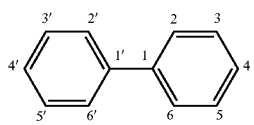

EXAMPLE 1

Compound 1

2-(methylamino)-2-oxoethyl {2-[(4-chlorophenyl)-oxy]ethyl}carbamate

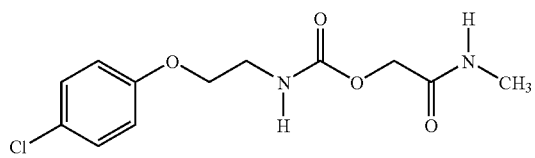

1.1 ethyl[(phenyloxycarbonyl)oxy]acetate

A solution of 25 g (240 mmol) of ethyl glycolate and of 55 ml (315 mmol) of diisopropylethylamine in 500 ml of toluene is admixed slowly at ambient temperature with 32 ml (256 mmol) of phenyl chloroformate. Stirring is continued at ambient temperature for 2 hours. The salt formed is separated off and the filtrate is concentrated under reduced pressure. This gives 53.7 g of oily product, used as it is in the following step.

1.2. ethyl {[({2-[(4-chlorophenyl)oxy]ethyl}-amino) carbonyl]oxy}acetate

A solution of 0.6 g (3.5 mmol) of [(4-chloro-phenyl)oxy] ethylamine (Chim. Ther. 1973, 8, 259-270) and 1.3 g (5.8 mmol) of ethyl [(phenyloxy-carbonyl)oxy]acetate, prepared in Step 1.1., in 30 ml of toluene is heated at 60° C. overnight. It is evaporated to dryness and the product is purified by chromatography on silica gel, eluting with a 30/70 mixture of ethyl acetate and cyclohexane. This gives 0.7 g of oily product, containing ~10% of cyclized oxazolidine dione product, used as it is in the following step.

1.3. 2-(methylamino)-2-oxoethyl {2-[(4-chlorophenyl)oxy]ethyl}carbamate 3.5 ml (7 mmol) of a 2M solution of methylamine in tetrahydrofuran are added to a solution of 0.7 g (2.3 mmol) of ethyl{[({2-[(4-chlorophenyl)-oxy]ethyl}amino)carbonyl] oxy}acetate, prepared in Step 1.2., in 5 ml of methanol. The mixture is left to react at ambient temperature overnight. It is evaporated to dryness and the residual solid is washed with hexane and then with diisopropyl ether, to give 0.59 g of product in powder form.

Melting point (° C.): 147-149 LC-MS: M+H=287 ¹H NMR (DMSO) δ(ppm): 7.75 (m, 1H), 7.40 (m, 1H), 7.25 (d, 2H), 6.95 (d, 2H), 4.35 (s, 2H), 3.95 (t, 2H), 3.35 (m, 2H), 2.60 (d, 3H).

EXAMPLE 2

Compound 11

2-amino-2-oxoethyl(2-[(4-cyanophenyl)oxy]ethyl)-carbamate 2.1 3-(2-hydroxyethyl)-1,3-oxazolidine-2,4-dione

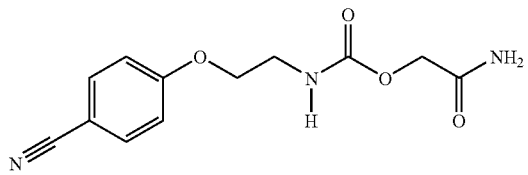

A solution of 3 ml (39.6 mmol) of methyl glycolate in 25 ml of tetrahydrofuran is added dropwise over 2 hours to a solution of 49 ml (95 mmol) of phosgene, 1.9M in toluene, which is diluted in 50 ml of tetrahydrofuran and cooled using an ice bath. The mixture is subsequently stirred at ambient temperature for 16 hours and evaporated to dryness. Coevaporation is carried out 4 times with 30 ml of dichloromethane. The residue is taken up with 40 ml of acetonitrile and added dropwise over 1 hour to a solution of 3.4 ml (59.4 mmol) of ethanolamine and 30 ml (178 mmol) of diisopropylethylamine in a 50/10 mixture of acetonitrile and dichloromethane, cooled using an ice bath. The mixture is subsequently stirred at ambient temperature for 16 hours. It is filtered over celite and evaporated to dryness and the product is purified by chromatography on silica gel, eluting with a 70/30 then 80/20 mixture of ethyl acetate and n-hexane, to give 4.9 g of product in white solid form.

2.2. 2-amino-2-oxoethyl(2-[(4-cyanophenyl)-oxy]ethyl)carbamate 0.61 ml (1.35 mmol) of a 2.2M solution of diethyl azodicarboxylate in toluene is added dropwise to a solution of 0.13 g (0.88 mmol) of 3-(2-hydroxyethyl)-1,3-oxazolidine-2,4-dione, prepared in Step 2.1., 0.35 g (1.35 mmol) of triphenylphosphine and 0.10 g (0.89 mmol) of 4-hydroxybenzonitrile in 2 ml of benzene, cooled using an ice bath. The reaction mixture is subsequently stirred at ambient temperature for 16 hours. It is evaporated to dryness and the product is purified by chromatography on silica gel, eluting with a 99/1 then 98/2 mixture of dichloromethane and ethyl acetate. The product is taken up in 1.5 ml of a 7M solution of ammonia (10.5 mmol) in methanol. This solution is stirred for one hour. The precipitate is filtered off and washed with ethyl acetate, to give 0.035 g of white solid.

Melting point (° C.): 204-206 LC-MS: M+H=264 ¹H NMR (DMSO) δ(ppm): 7.55 (d, 2H), 7.05 (m, 1H), 6.90-6.80 (m+d, 4H), 4.35 (s, 2H), 4.05 (t, 2H), 3.45 (m, 2H)

EXAMPLE 3

Compound 58

2-amino-2-oxoethyl [4-(1-naphthalenyloxy]butyl]-carbamate

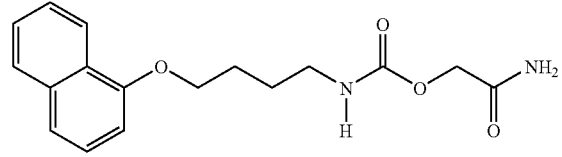

3.1. 3-[4-(1-naphthalenyloxy]butyl]-1,3-oxazolidine-2,4-dione

A solution of 3.1 g (11.1 mmol) of 1-[(4-bromobutyl)oxy] naphthalene (Eur. J. Med. Chem. 1997, 32, 175-179) and 1.35 g (13.3 mmol) of 1,3-oxazolidine-2,4-dione (J. Med. Chem. 1991, 34, 1542-1543) in 30 ml of tetrahydrofuran is admixed dropwise with a solution of 2.55 g (22.2 mmol) of 1,1,3,3-tetramethylguanidine in 15 ml of tetrahydrofuran. The mixture is heated at reflux for 8 hours. 0.28 g (2.7 mmol) of 1,3-oxazolidine-2,4-dione and 0.32 g (2.7 mmol) of 1,1,3,3-tetramethylguanidine are added and the mixture is heated at reflux for 4 more hours. The reaction mixture is cooled using an ice bath, and 100 ml of ethyl acetate and then 50 ml of 1M aqueous hydrochloric acid are added. The system is decanted and the aqueous phase is extracted with 2×80 ml of ethyl acetate. The organic phases are subsequently washed with 80 ml of water and then with 80 ml of saturated aqueous sodium chloride solution. They are dried over sodium sulfate and then evaporated to dryness. The product is purified by chromatography on silica gel, eluting with an 80/20 mixture of cyclohexane and ethyl acetate, to give 2.0 g of product, which is used as it is in the following step.

3.2. 2-amino-2-oxoethyl [4-(1-naphthalenyl-oxy)butyl]carbamate 1.50 g (5.0 mmol) of 3-[4-(1-naphthalenyl-oxy)butyl]-1,3-oxazolidine-2,4-dione, prepared in Step 3.1., are dissolved in a mixture of 10 ml of tetrahydrofuran and 28 ml of a 7N solution of ammonia (200 mmol) in methanol. The solution is left to react overnight at ambient temperature and then evaporated to dryness. The product is purified by chromatography on silica gel, eluting with a 97/3 mixture of dichloromethane and methanol. It is recrystallized from ethyl acetate and then washed with diethyl ether, to give 0.73 g of product in white solid form.

Melting point (° C.): 80-82 LC-MS: M+H=317 ¹H NMR (CDCl₃) δ(ppm): 8.25 (dd, 1H), 7.80 (dd, 1H), 7.55-7.30 (m, 4H), 6.80 (d, 1H), 6.00 (m, 1H), 5.65 (m, 1H), 5.05 (m, 1H), 4.65 (s, 2H), 4.20 (t, 2H), 3.35 (m, 2H), 2.00 (m, 2H), 1.90 (m, 2H)

EXAMPLE 4

Compound 85

2-(methylamino)-2-oxoethyl 4-[(4'-fluoro-4-biphenyl)-oxy]-1-piperidinecarboxylate

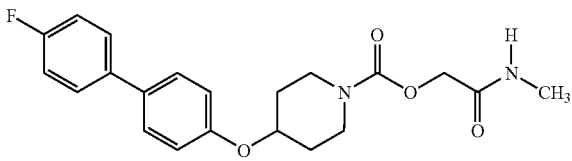

4.1. 1,1-dimethylethyl 4-[(4-bromophenyl)-oxy]-1-piperidinecarboxylate

A solution of 2.01 g (10 mmol) of 1,1-dimethylethyl 4-hydroxy-1-piperidinecarboxylate in 20 ml of dimethylformamide is admixed with 7 g (40 mmol) of 1-bromo-4-fluorobenzene and 2.5 g (50 mmol) of sodium hydride at 50% in mineral oil. The mixture is stirred at 100° C. for 3 hours and then evaporated to dryness. The residue is taken up in 50 ml of ice-water and extracted with dichloromethane. The organic extracts are evaporated to dryness, to give 3.5 g of an oily product, which is used as it is in the following step.

4.2. 4-[(4-bromophenyl)oxy]piperidine

A solution of 3.5 g (9.83 mmol) of 1,1-dimethylethyl 4-[(4-bromophenyl)oxy]-1-piperidinecarbooxylate, prepared in Step 4.1., in 20 ml of dichloromethane is admixed with 10 ml of trifluoroacetic acid and the solution is stirred at ambient temperature for 1 hour. It is evaporated to dryness and then the residue is taken up in 30 ml of toluene, which is evaporated again to dryness. The residue is subsequently washed with pentane and then taken up in a mixture of 60 ml of dichloromethane and 20 ml of 4N aqueous ammonia solution. It is stirred vigorously for 15 minutes and then the organic phase is decanted, dried over sodium sulfate and evaporated to dryness, to give 2.7 g of product in oil form, which is used as it is in the following step.

4.3. 2-(ethyloxy)-2-oxoethyl 4-[(4-bromo-phenyl)oxy]-1-piperidinecarboxylate 2.7 g (7.58 mmol) of 4-[(4-bromophenyl)-oxy]piperidine, prepared in Step 4.2., and 1.70 g (7.6 mmol) of ethyl {[(phenyloxy)carbonyl]oxy}acetate, prepared in accordance with Example 1.1, are mixed in 40 ml of toluene and the solution is heated at 50° C. for 20 hours. After cooling, it is evaporated to dryness and the product is purified by chromatography on silica gel, eluting with a 40/60 mixture of ethyl acetate and cyclohexane. The eluate is subsequently triturated in diisopropyl ether, to give 2.9 g of product in powder form.

Melting point (° C.): 87-88

4.4. 2-(methylamino)-2-oxoethyl 4-[(4-bromophenyl)oxy]-1-piperidinecarboxylate 2.9 g (7.5 mmol) of 2-(ethyloxy)-2-oxoethyl 4-[(4-bromophenyl)oxy]-1-piperidinecarboxylate, prepared in Step 4.3., in solution in 10 ml of a 33% ethanolic solution of methylamine are stirred at ambient temperature for 20 hours. Following evaporation, the product is purified by chromatography on silica gel, eluting with ethyl acetate, to give 0.8 g of product in gum form, which is used as it is in the following step.

4.5. 2-(methylamino)-2-oxoethyl 4-[(4'-fluoro-4-biphenyl)oxy]-1-piperidinecarboxylate 0.1 g (0.27 mmol) of 2-(methylamino)-2-oxoethyl 4-[(4-bromophenyl)oxy]-1-piperidinecarbooxylate, prepared in Step 4.4., 0.01 g of tetrakis(triphenylphosphine)palladium(0) and 0.057 g (0.4 mmol) of 4-fluorophenylboronic acid are placed in a glass tube with stopper. 4 ml of toluene, 2 ml of a 2N aqueous solution of sodium carbonate and 0.5 ml of ethanol are added. The mixture is heated at 80° C. with stirring for 2 hours. After it has cooled, 1 ml of water and 2 ml of toluene are added. The organic phase is withdrawn and the product is purified by chromatography on silica gel, eluting with a 95/5 mixture of dichloromethane and methanol. The product is redissolved in 1 ml of ethanol and then reprecipitated by adding 2 ml of water, to give 0.031 g of product in powder form.

Melting point (° C.): 117-119 LC-MS: M+H 387 $^1$H NMR (CDCl$_3$) δ(ppm): 7.70 (dd, 2H), 7.65 (d, 2H), 7.30 (dd, 2H), 7.20 (d, 2H), 6.25 (broad s, 1H), 4.80 (s+m, 3H), 4.00-3.70 (m, 4H), 3.05 (d, 3H), 2.25-2.00 (m, 4H)

EXAMPLE 5

Compound 120

2-(methylamino)-2-oxoethyl 4-{[(4-bromophenyl)oxy]-methyl}-1-piperidinecarboxylate

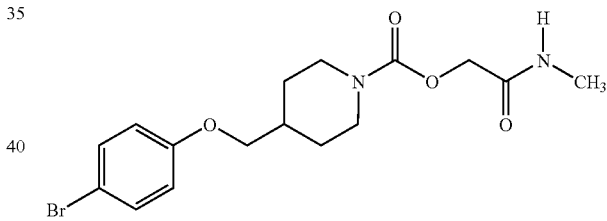

5.1. 1,1-dimethylethyl 4-{[(4-bromophenyl)-oxy]methyl}-1-piperidinecarboxylate The procedure described in Example 4.1. is repeated. Starting from 2.5 g (11.6 mmol) of 1,1-dimethylethyl 4-(hydroxymethyl)-1-piperidinecarbooxylate and 8.13 g (46.4 mmol) of 1-bromo-4-fluorobenzene gives 5.75 g of crude product in oil form.

5.2. 4-{[(4-bromophenyl)oxy]methyl}piperidine

The procedure described in Example 4.2 is repeated. Starting from 5.75 g of 1,1-dimethylethyl 4-{[(4-bromophenyl)oxy]methyl}-1-piperidinecarboxylate, prepared in Step 5.1, gives 3 g of product in oil form.

5.3. 2-(ethyloxy)-2-oxoethyl 4-{[(4-bromophenyl)oxy]methyl}-1-piperidinecarboxylate The procedure described in Example 4.3. is repeated. Starting from 1.6 g (5.9 mmol) of 4-{[(4-bromophenyl)oxy]methyl}piperidine, prepared in Step 5.2., and from 1.32 g (5.9 mmol) of ethyl {[(phenyloxy)carbonyl]oxy}acetate, prepared in accordance with Example 1.1., gives the product in oil form.

5.4. 2-(methylamino)-2-oxoethyl 4-{[(4-bromophenyl)oxy]methyl}-1-piperidinecarboxylate The procedure described in Example 4.4. is repeated. Starting from 2-(ethyloxy)-2-oxoethyl 4-{[(4-bromophenyl)oxy]methyl}-1-piperidinecarboxylate, prepared in Step 5.3, gives 1.1 g of product in powder form.

Melting point (° C.): 163-165 LC-MS: M+H=386 $^1$H NMR (CDCl$_3$) δ(ppm): 7.35 (d, 2H), 6.75 (d, 2H), 6.05 (broad s, 1H), 4.70-4.50 (m, 2H), 4.30-4.10 (m, 2H), 3.80 (d, 2H), 3.00-2.75 (m, 2H), 2.85 (d, 3H), 2.10-1.80 (m, 3H), 1.45-1.20 (m, 2H)

EXAMPLE 6

Compound 154

2-(methylamino)-2-oxoethyl 4-{[(4'-(trifluoromethyl)-4-biphenyl)oxy]methyl}-1-piperidinecarboxylate

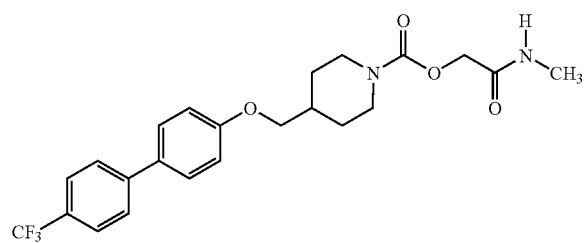

The procedure described in Example 4.5. is repeated. Starting from 0.1 g (0,26 mmol) of 2-(methylamino)-2-oxoethyl 4-{[(4-bromophenyl)oxy]methyl}-1-piperidinecarbooxylate, prepared in accordance with Example 5, and from 0.074 g (0.389 mmol) of 4-trifluoromethylphenyl-boronic acid gives 0.049 g of product in powder form.

Melting point (° C.): 197-199 LC-MS: M+H=451 $^1$H NMR (DMSO) δ(ppm): 7.85-7.65 (m, 7H), 7.05 (d, 2H), 4.35 (s, 2H), 4.05 (broad d, 2H), 3.90 (d, 2H), 2.85 (m, 2H), 2.60 (d, 3H), 2.00 (m, 1H), 1.80 (broad d, 2H), 1.35-1.10 (m, 2H).

EXAMPLE 7

Compound 137

2-amino-2-oxoethyl 4-[(1-naphthalenyloxy)methyl]-1-piperidinecarboxylate

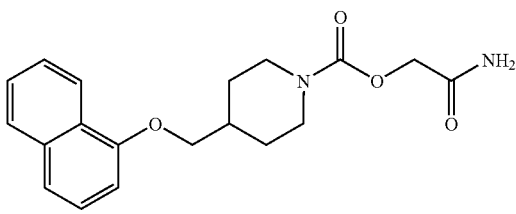

7.1. 1,1-dimethylethyl 4-[(1-naphthalenyl-oxy)methyl]-1-piperidinecarboxylate A solution of 5.0 g (23.2 mmol) of 1,1-dimethylethyl 4-(hydroxymethyl)-1-piperidinecarbooxylate, 4.3 g (29.8 mmol) of 1-naphthalenol and 7.82 g (29.8 mmol) of triphenylphosphine in 120 ml of tetrahydrofuran, cooled under nitrogen by means of an ice bath, is admixed dropwise with a solution of 6.03 g (29.8 mmol) of diisopropyl azodicarboxylate. The reaction mixture is allowed to return to ambient temperature and stirring is continued overnight. 2 ml of methanol are added and then the mixture is evaporated to dryness. The residue is taken up in 200 ml of dichloromethane and washed in succession with a 10% aqueous potassium hydrogen sulfate solution, water and a 1M aqueous solution of sodium hydroxide. The system is dried over sodium sulfate and evaporated to dryness. The product is purified by chromatography on silica gel, eluting with an 80/20 then 70/30 and 50/50 mixture of cyclohexane and dichloromethane, to give 7.96 g of product in oil form, which solidifies.

Melting point (° C): 97-100

7.2. 4-[(1-naphthalenyloxy)methyl]piperidine

A solution of 7.96 g (29.1 mmol) of 1,1-dimethylethyl 4-[(1-naphthalenyloxy)methyl]-1-piperidinecarboxylate, prepared in Step 7.1., in 120 ml of methanol and 28 ml of 35% aqueous hydrochloric acid is heated at 60° C. for 6 hours. It is cooled to ambient temperature and evaporated to dryness, and then coevaporation is carried out twice with ethanol. The solid residue is washed with diethyl ether and then dried under vacuum in the presence of phosphorus pentoxide, to give 3.1 g of white solid.

The solid is taken up in 80 ml of water and a 30% aqueous sodium hydroxide solution is added until a basic pH is obtained, after which the system is extracted twice with 150 ml of diethyl ether. The extracts are dried over sodium sulfate and concentrated to dryness, to give 2.75 g of oily product, which is used as it is in the following step.

7.3. 2-(ethyloxy)-2-oxoethyl 4-[(1-naphthalenyloxy)methyl]-1-piperidinecarboxylate A solution of 2.75 g (11.4 mmol) of 4-[(1-naphthalenyloxy)methyl]piperidine, prepared in Step 7.2., and 2.56 g (11.4 mmol) of ethyl [(phenyloxy-carbonyl)oxy]acetate, prepared in accordance with Example 1.1, in 80 ml of toluene is heated at 50° C. overnight. It is evaporated to dryness and the residue is taken up in a mixture of water, dichloromethane and saturated aqueous sodium hydrogen carbonate solution. The organic phase is decanted, dried over sodium sulfate and evaporated to dryness. The product is purified by chromatography on silica gel, eluting with a 50/50 mixture of cyclohexane and dichloromethane and then with dichloromethane and with a 95/5 mixture of dichloromethane and ethyl acetate. This gives 2.05 g of product in oil form, which is used as it is in the following step.

7.4. 2-amino-2-oxoethyl 4-[(1-naphthalenyl-oxy)methyl]-1-piperidinecarboxylate 1.0 g (2.69 mmol) of 2-(ethyloxy)-2-oxoethyl 4-[(1-naphthalenyloxy)methyl]-1-piperidinecarboxylate, prepared in Step 7.3., is dissolved in 12 ml of a 7N solution of ammonia (84 mmol) in methanol. The solution is left to react at ambient temperature for 3 days. It is evaporated to dryness and the residue is purified by chromatography on silica gel, eluting with a 90/10 then 80/20, 70/30 and 50/50 mixture of dichloromethane and ethyl acetate and then with a 95/5 mixture of ethyl acetate and methanol. The eluate is subsequently recrystallized from ethyl acetate, to give 0.77 g of product.

Melting point (° C.): 135-136 LC-MS: M+H=343 ¹H NMR (DMSO) δ(ppm): 8.15 (dd, 1H), 7.80 (dd, 1H), 7.50-7.30 (m, 4H), 7.30 (m, 1H), 7.15 (m, 1H), 6.95 (d, 1H), 4.35 (s, 2H), 4.15-4.00 (m+d, 4H), 4.90 (m, 2H), 2.10 (m, 1H), 1.90 (d, 2H), 1.45-1.25 (m, 2H)

EXAMPLE 8

Compound 148

2-amino-2-oxoethyl 4-[(7-quinolinyloxy)methyl]-1-piperidinecarboxylate

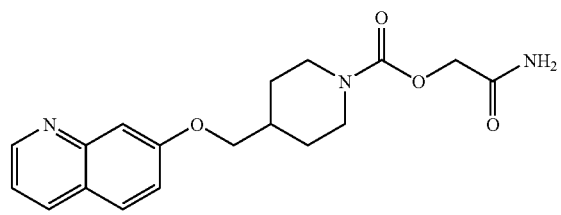

8.1. 2-(methyloxy)-2-oxoethyl 4-(hydroxymethyl)-1-piperidinecarboxylate

The procedure described in Example 2.1. is repeated, using 6.84 g (59.4 mmol) of 4-(hydroxy-methyl)piperidine, in place of ethanolamine, to give 7.85 g of product in colorless oil form.

8.2. 2-amino-2-oxoethyl 4-[(7-quinolinyl-oxy)methyl]-1-piperidinecarboxylate 0.26 g (1.03 mmol) of 1,1'-(azodicarbonyl)-dipiperidine (ADDP) is added to a solution of 0.16 g (0.69 mmol) of 2-(methyloxy)-2-oxoethyl 4-(hydroxymethyl)-1-piperidinecarboxylate, prepared in Step 8.1., 0.26 ml (1.03 mmol) of tri-n-butylphosphine and 0.13 g (0.90 mmol) of 7-hydroxyquinoline in 2.5 ml of benzene, which is cooled by means of an ice bath. The mixture is stirred at 0° C. for 15 minutes and then at ambient temperature for 16 hours. It is filtered over celite and rinsed with diethyl ether. The filtrates are evaporated to dryness and purified by chromatography on silica gel, eluting with a 70/30 mixture of ethyl acetate in n-hexane. The product obtained is dissolved in 3 ml (21 mmol) of a 7M solution of ammonia in methanol. The solution is stirred for 3 hours and then evaporated to dryness. The product is purified by chromatography on silica gel, eluting with a 90/10 mixture of ethyl acetate in ethanol, and recrystallized from ethyl acetate, to give 0.115 g of product in white solid form.

Melting point (° C.): 137-139 LC-MS: M+H=344 ¹H NMR (CDCl₃) δ(ppm): 7.80 (dd, 1H), 8.05 (dd, 1H), 7.70 (d, 1H), 7.40 (d, 1H), 7.30-7.15 (m, 2H), 6.05 (m, 1H), 5.65 (m, 1H), 4.60 (s, 2H), 4.25 (m, 2H), 4.00 (d, 2H), 2.90 (m, 2H), 2.10 (m, 1H), 1.95 (d, 2H), 1.50-1.30 (m, 2H)

EXAMPLE 9

Compound 168

2-(methylamino)-2-oxoethyl 4-{2-[(4-bromophenyl)-oxy]ethyl}-1-piperidinecarboxylate

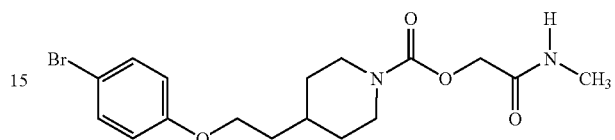

9.1. 1,1-dimethylethyl 4-{2-[(4-bromophenyl)-oxy]ethyl}-1-piperidinecarboxylate The procedure described in Example 4.1. is repeated. Starting from 1.93 g (8.4 mmol) of 1,1-dimethylethyl 4-(2-hydroxyethyl)-1-piperidinecarbooxylate and 5.88 g (33.6 mmol) of 1-bromo-4-fluorobenzene gives 4.1 g of crude product in oil form.

9.2. 4-{2-[(4-bromophenyl)oxy]ethyl}-piperidine

The procedure described in Example 4.2. is repeated. Starting from 1,1-dimethylethyl 4-{2-[(4-bromophenyl)oxy]ethyl}-1-piperidinecarboxylate, prepared in Step 9.1., gives 1.79 g of product in powder form.

Melting point (° C.): 100-102

9.3. 2-(ethyloxy)-2-oxoethyl 4-{2-[(4-bromophenyl)oxy]ethyl}-1-piperidinecarboxylate The procedure described in Example 4.3. is repeated. Starting from 1.76 g (6.19 mmol) of 4-{2-[(4 bromophenyl)oxy]ethyl} prepared in Step 9.2., and 1.39 g (6.19 mmol) of ethyl {[(phenyloxy)carbonyl]oxy}-acetate, prepared in accordance with Example 1.1., gives 1.4 g of product in oil form.

9.4. 2-(methylamino)-2-oxoethyl 4-{2-[(4-bromophenyl)oxy]ethyl}-1-piperidinecarboxylate The procedure described in Example 4.4. is repeated. Starting from 1.3 g (3.14 mmol) of 2-(ethyloxy)-2-oxoethyl 4-{2-[(4-bromophenyl)oxy]ethyl}-1-piperidinecarboxylate, prepared in Step 9.3., gives 0.95 g of product in powder form.

Melting point (° C.): 101-103 LC-MS: M+H=400 ¹H NMR (CDCl₃) δ(ppm): 7.55 (d, 2H), 7.00 (d, 2H), 6.25 (broad s, NH), 4.90-4.70 (m, 2H), 4.50-4.25 (m, 2H), 4.20 (t, 2H), 3.20-2.90 (m, 2H), 3.10 (d, 3H), 2.05-1.90 (m, 5H), 1.55-1.30 (m, 2H)

EXAMPLE 10

Compound 186

2-(methylamino)-2-oxoethyl 4-{2-[(4'-chloro-4-biphenyl)oxy]ethyl}-1-piperidinecarboxylate The procedure described in Example 4.5 is

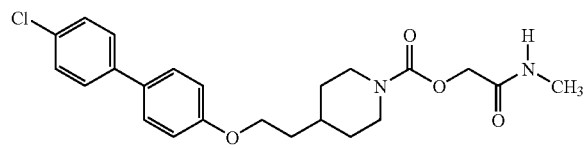

repeated. Starting from 0.1 g (0.25 mmol) of 2-(methylamino)-2-oxoethyl 4-{2-[(4-bromophenyl)-oxy]ethyl}-1-piperidinecarboxylate, prepared in accordance with Example 9, and 0.117 g (0.75 mmol) of 4-chlorophenylboronic acid gives 0.087 g of product in powder form.

Melting point (° C.): 104-106 LC-MS: M+H=431 $^1$H NMR (CDCl$_3$) δ(ppm): 7.70-7.50 (m, 6H), 7.10 (d, 2H) 6.20 (broad s, NH), 4.85-4.60 (m, 2H), 4.45-4.15 (m, 2H), 4.20 (t, 2H), 3.15-2.95 (m, 2H), 3.05 (d, 3H), 2.10-1.85 (m, 5H), 1.50-1.25 (m, 2H)

EXAMPLE 11

Compound 183

2-amino-2-oxoethyl 4-[2-(7-isoquinolinyloxy)ethyl]-1-piperidinecarbamate

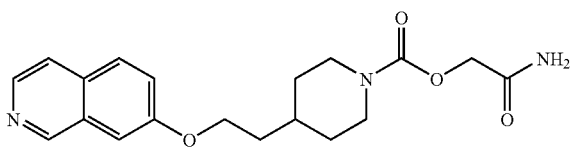

11.1. 2-(methyloxy)-2-oxoethyl 4-(2-hydroxyethyl)-1-piperidinecarboxylate

The procedure described in Example 2.1. is repeated, using 7.6 g (59.4 mmol) of 4-(2-hydroxy-ethyl)piperidine, in place of ethanolamine, to give 7.1 g of product in colorless oil form.

11.2. 2-amino-2-oxoethyl 4-[2-(7-isoquinolinyloxy)ethyl]-1-piperidinecarbamate The procedure described in Example 8.2. is repeated, starting from 0.46 g (1.84 mmol) of ADDP, 0.30 g (1.24 mmol) of 2-(methyloxy)-2-oxoethyl 4-(2-hydroxyethyl)-1-piperidinecarboxylate, prepared in Step 11.1., 0.46 ml of tri-n-butylphosphine and 0.26 g (1.84 mmol) of 7-hydroxyisoquinoline in 4 ml of benzene. The product is purified by chromatography on silica gel, eluting with ethyl acetate and then with a 95/5 mixture of ethyl acetate and ethanol, to give 0.25 g of product in white solid form.

Melting point (° C.): 179-181 LC-MS: M+H=358 $^1$H NMR (CDCl$_3$) δ(ppm): 9.15 (s, 1H), 8.45 (d, 1H), 7.60 (d, 1H), 7.35 (dd, 1H), 7.20 (d, 1H), 6.05 (m, 1H), 5.75 (m, 1H), 4.60 (s, 2H), 4.20 (t, 4H), 2.90 (m, 2H), 1.90-1.70 (m, 5H), 1.40-1.20 (m, 2H)

EXAMPLE 12

Compound 83

2-amino-2-oxoethyl 3-[(1-naphthalenyloxy)methyl]-1-pyrrolidinecarboxylate

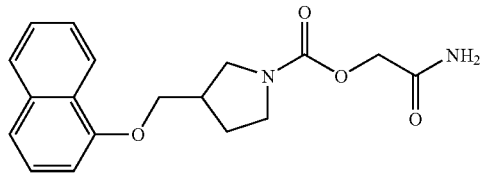

12.1. 1,1-dimethylethyl 3-[(1-naphthalenyl-oxy)methyl]-1-pyrrolidinecarboxylate A solution of 1.0 g (4.9 mmol) of 1,1-dimethylethyl 3-(hydroxymethyl)-1-pyrrolidinecarbooxylate (described in WO 0066557), 0.95 g (6.4 mmol) of 1-naphthalenol and 1.4 g (6.9 mmol) of tri-n-butylphosphine in 40 ml of toluene and 20 ml of tetrahydrofuran, cooled under nitrogen by means of an ice bath, is admixed dropwise with a solution of 1.74 g (6.9 mmol) of ADDP. The reaction mixture is allowed to return to ambient temperature and stirring is continued for 24 hours. The mixture is filtered and the precipitate is rinsed with toluene. It is evaporated to dryness. The residue is taken up in dichloromethane and washed with a 1M aqueous sodium hydroxide solution. It is dried over sodium sulfate and evaporated to dryness. The residue is purified by chromatography on a silica gel column, eluting with dichloromethane and then with a 98/2 mixture of dichloromethane and methanol, to give 0.80 g of product in colorless oil form.

12.2. 3-[(1-naphthalenyloxy)methyl]-pyrrolidine

A solution of 0.42 g (1.28 mmol) of 1,1-dimethylethyl 3-[(1-naphthalenyloxy)methyl]-1-pyrrolidinecarboxylate, prepared in Step 12.1., in 10 ml of 1,4-dioxane and 6 ml of a 2N solution of aqueous hydrochloric acid is stirred for 6 hours. It is evaporated to dryness and then coevaporation is carried out twice with toluene. The solid residue is washed with diethyl ether. The solid is taken up in dichloromethane and concentrated ammonia solution is added until a basic pH is obtained. The system is filtered on a Whatman PTFE cartridge and the organic phase is concentrated, to give 0.21 g of oily product, which is used as it is in the following step.

12.3. 2-(ethyloxy)-2-oxoethyl 3-[(1-naphthalenyloxy)methyl]-1-pyrrolidinecarboxylate A solution of 0.20 g (0.88 mmol) of 3-[(1-naphthalenyloxy)methyl]pyrrolidine, prepared in Step 12.2., and 0.35 g (1.5 mmol) of ethyl [(phenyloxycarbonyl)oxy]acetate, prepared in accordance with Example 1.1, in 6 ml of toluene is heated at 60° C. overnight. It is evaporated to dryness and the residue is taken up in a mixture of water, dichloromethane and saturated aqueous sodium hydrogen carbonate solution. The organic phase is decanted, dried over sodium sulfate and evaporated to dryness. The residue is purified by chromatography on a silica gel column, eluting with dichloromethane and then with a 99/1 mixture of dichloromethane and methanol. This gives 0.24 g of product in oil form, which is used as it is in the following step.

12.4. 2-amino-2-oxoethyl 3-[(1-napthalenyl-oxy)methyl]-1-pyrrolidinecarboxylate 0.24 g (0.67 mmol) of 2-(ethyloxy)-2-oxoethyl 3-[(1-naphthenyloxy)methyl]-1-pyrrolidinecarboxylate, prepared in Step 12.3., is dissolved in 15 ml of a 7N solution of ammonia (105 mmol) in methanol. The solution is stirred in a stoppered tube at ambient temperature for 3 days. It is evaporated to dryness and the residue is purified by chromatography on a silica gel column, eluting with a 97/3 then 94/6 mixture of dichloromethane and methanol. The solid obtained is triturated in diethyl ether and filtered, to give 0.15 g of product.

Melting point (° C.): 161-163 LC-MS: M+H=329 $^1$H NMR (DMSO) δ(ppm): 8.15 (m, 1H), 7.75 (m, 1H), 7.50-7.30 (m, 4H), 7.10-6.90 (s, 2H), 6.80 (m, 1H), 4.40 (s, 2H), 4.20-4.05 (m, 2H), 3.90-3.30 (m, 4H), 2.90-2.70 (m, 1H), 2.30-2.10 (m, 1H), 2.05-1.85 (m, 1H).

The table which follows lists the chemical structures and the physical properties of some compounds according to the invention.

TABLE

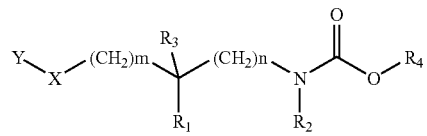

(I)

| Cpd | Y | X | m | n | $R_1$ | $R_2$ | $R_3$ | $R_4$ | m.p. ° C. (or M + H) |
|---|---|---|---|---|---|---|---|---|---|
| 1. | 4-chlorophenyl | O | 0 | 1 | H | H | H | $CH_2CONHCH_3$ | 147-149 |
| 2. | 4-chlorophenyl | O | 0 | 1 | H | H | H | $CH_2CONH_2$ | 128-130 |
| 3. | 4-chlorophenyl | O | 0 | 2 | H | H | H | $CH_2CONH_2$ | 108-110 |
| 4. | 4-chlorophenyl | O | 0 | 3 | H | H | H | $CH_2CONH_2$ | 116-118 |
| 5. | 3-chlorophenyl | O | 0 | 1 | H | H | H | $CH_2CONH_2$ | 114-116 |
| 6. | 3-chlorophenyl | O | 0 | 2 | H | H | H | $CH_2CONH_2$ | 90-92 |
| 7. | 3-chlorophenyl | O | 0 | 3 | H | H | H | $CH_2CONH_2$ | 114-116 |
| 8. | 2-chlorophenyl | O | 0 | 1 | H | H | H | $CH_2CONH_2$ | 128-130 |
| 9. | 2-chlorophenyl | O | 0 | 2 | H | H | H | $CH_2CONH_2$ | 128-130 |
| 10. | 2-chlorophenyl | O | 0 | 3 | H | H | H | $CH_2CONH_2$ | 110-112 |
| 11. | 4-cyanophenyl | O | 0 | 1 | H | H | H | $CH_2CONH_2$ | 204-206 |
| 12. | 4-cyanophenyl | O | 0 | 2 | H | H | H | $CH_2CONH_2$ | 173-175 |
| 13. | 4-cyanophenyl | O | 0 | 3 | H | H | H | $CH_2CONH_2$ | 169-171 |
| 14. | 3-cyanophenyl | O | 0 | 1 | H | H | H | $CH_2CONH_2$ | 142-143 |
| 15. | 3-cyanophenyl | O | 0 | 2 | H | H | H | $CH_2CONH_2$ | 129-131 |
| 16. | 3-cyanophenyl | O | 0 | 3 | H | H | H | $CH_2CONH_2$ | 123-125 |
| 17. | 4-iso-propylphenyl | O | 0 | 1 | H | H | H | $CH_2CONH_2$ | 95-97 |
| 18. | 4-iso-propylphenyl | O | 0 | 2 | H | H | H | $CH_2CONH_2$ | (295) |
| 19. | 4-iso-propylphenyl | O | 0 | 3 | H | H | H | $CH_2CONH_2$ | 103-105 |
| 20. | 3-iso-propylphenyl | O | 0 | 1 | H | H | H | $CH_2CONH_2$ | 96-98 |
| 21. | 3-iso-propylphenyl | O | 0 | 2 | H | H | H | $CH_2CONH_2$ | (295) |
| 22. | 3-iso-propylphenyl | O | 0 | 3 | H | H | H | $CH_2CONH_2$ | 88-90 |
| 23. | 4-tert-butylphenyl | O | 0 | 2 | H | H | H | $CH_2CONH_2$ | 90-92 |
| 24. | 4-tert-butylphenyl | O | 0 | 3 | H | H | H | $CH_2CONH_2$ | (323) |
| 25. | 3-tert-butylphenyl | O | 0 | 2 | H | H | H | $CH_2CONH_2$ | (309) |
| 26. | 3-tert-butylphenyl | O | 0 | 3 | H | H | H | $CH_2CONH_2$ | (323) |
| 27. | 4-(1,1,3,3-tetramethylbutyl)phenyl | O | 0 | 2 | H | H | H | $CH_2CONH_2$ | (365) |
| 28. | 4-(1,1,3,3-tetramethylbutyl)phenyl | O | 0 | 3 | H | H | H | $CH_2CONH_2$ | (379) |
| 29. | 4-(1,1-dimethylphenylmethyl)phenyl | O | 0 | 1 | H | H | H | $CH_2CONH_2$ | (357) |
| 30. | 4-(1,1-dimethylphenylmethyl)phenyl | O | 0 | 2 | H | H | H | $CH_2CONH_2$ | (371) |
| 31. | 4-(1,1-dimethylphenylmethyl)phenyl | O | 0 | 3 | H | H | H | $CH_2CONH_2$ | (385) |
| 32. | 4-phenylphenyl | O | 0 | 1 | H | H | H | $CH_2CONH_2$ | 196-198 |
| 33. | 4-phenylphenyl | O | 0 | 2 | H | H | H | $CH_2CONH_2$ | 187-189 |
| 34. | 4-phenylphenyl | O | 0 | 3 | H | H | H | $CH_2CONH_2$ | 192-194 |
| 35. | 4-(4-chlorophenyl)phenyl | O | 0 | 1 | H | H | H | $CH_2CONH_2$ | 193-195 |
| 36. | 4-(3-chlorophenyl)phenyl | O | 0 | 1 | H | H | H | $CH_2CONH_2$ | 168-170 |
| 37. | 4-(2-chlorophenyl)phenyl | O | 0 | 1 | H | H | H | $CH_2CONH_2$ | 114-116 |
| 38. | 4-(4-methoxyphenyl)phenyl | O | 0 | 1 | H | H | H | $CH_2CONH_2$ | 194-196 |
| 39. | 4-(3-methoxyphenyl)phenyl | O | 0 | 1 | H | H | H | $CH_2CONH_2$ | (345) |
| 40. | 4-(2-methoxyphenyl)phenyl | O | 0 | 1 | H | H | H | $CH_2CONH_2$ | 127-129 |
| 41. | 3-phenylphenyl | O | 0 | 1 | H | H | H | $CH_2CONH_2$ | 126-128 |
| 42. | 3-phenylphenyl | O | 0 | 2 | H | H | H | $CH_2CONH_2$ | 110-112 |
| 43. | 3-phenylphenyl | O | 0 | 3 | H | H | H | $CH_2CONH_2$ | 127-129 |
| 44. | 3-(4-chlorophenyl)phenyl | O | 0 | 1 | H | H | H | $CH_2CONH_2$ | 137-139 |
| 45. | 3-(3-chlorophenyl)phenyl | O | 0 | 1 | H | H | H | $CH_2CONH_2$ | 90-92 |
| 46. | 3-(2-chlorophneyl)phenyl | O | 0 | 1 | H | H | H | $CH_2CONH_2$ | 55-57 |
| 47. | 3-(4-methoxyphenyl)phenyl | O | 0 | 1 | H | H | H | $CH_2CONH_2$ | 168-170 |
| 48. | 3-(3-methoxyphenyl)phenyl | O | 0 | 1 | H | H | H | $CH_2CONH_2$ | 86-88 |
| 49. | 2-phenylphenyl | O | 0 | 1 | H | H | H | $CH_2CONH_2$ | 92-94 |
| 50. | 2-phenylphenyl | O | 0 | 2 | H | H | H | $CH_2CONH_2$ | (329) |

TABLE-continued $$Y-X-(CH_2)_m-C(R_1)(R_3)-(CH_2)_n-N(R_2)-C(=O)-O-R_4 \quad (I)$$

| Cpd | Y | X | m | n | R₁ | R₂ | R₃ | R₄ | m.p. °C. (or M + H) |
|---|---|---|---|---|---|---|---|---|---|
| 51. | 2-phenylphenyl | O | 0 | 3 | H | H | H | CH$_2$CONH$_2$ | (343) |
| 52. | 2-(4-chlorophenyl)phenyl | O | 0 | 1 | H | H | H | CH$_2$CONH$_2$ | 130-132 |
| 53. | 2-(3-chlorophenyl)phenyl | O | 0 | 1 | H | H | H | CH$_2$CONH$_2$ | 88-90 |
| 54. | 2-(2-chlorophenyl)phenyl | O | 0 | 1 | H | H | H | CH$_2$CONH$_2$ | (349) |
| 55. | 2-(4-methoxyphenyl)phenyl | O | 0 | 1 | H | H | H | CH$_2$CONH$_2$ | 74-76 |
| 56. | naphthalen-1-yl | O | 0 | 1 | H | H | H | CH$_2$CONH$_2$ | (289) |
| 57. | naphthalen-1-yl | O | 0 | 2 | H | H | H | CH$_2$CONH$_2$ | (303) |
| 58. | naphthalen-1-yl | O | 0 | 3 | H | H | H | CH$_2$CONH$_2$ | 80-82 |
| 59. | naphthalen-1-yl | O | 0 | 3 | H | H | H | CH$_2$CONHCH$_3$ | 90-92 |
| 60. | 4-chloronaphthalen-1-yl | O | 0 | 3 | H | H | H | CH$_2$CONH$_2$ | 142-144 |
| 61. | 4-chloronaphthalen-1-yl | O | 0 | 3 | H | H | H | CH$_2$CONHCH$_3$ | 108-110 |
| 62. | naphthalen-2-yl | O | 0 | 1 | H | H | H | CH$_2$CONH$_2$ | (289) |
| 63. | naphthalen-2-yl | O | 0 | 2 | H | H | H | CH$_2$CONH$_2$ | 158-160 |
| 64. | naphthalen-2-yl | O | 0 | 3 | H | H | H | CH$_2$CONH$_2$ | 171-173 |
| 65. | 4-phenoxyphenyl | O | 0 | 1 | H | H | H | CH$_2$CONH$_2$ | 158-160 |
| 66. | 4-phenoxyphenyl | O | 0 | 2 | H | H | H | CH$_2$CONH$_2$ | 141-143 |
| 67. | 4-phenoxyphenyl | O | 0 | 3 | H | H | H | CH$_2$CONH$_2$ | 144-146 |
| 68. | pyridin-3-yl | O | 0 | 1 | H | H | H | CH$_2$OCNH$_2$ | 135-137 |
| 69. | pyridin-3-yl | O | 0 | 2 | H | H | H | CH$_2$CONH$_2$ | 119-121 |
| 70. | pyridin-3-yl | O | 0 | 3 | H | H | H | CH$_2$CONH$_2$ | 96-98 |
| 71. | 5-chloroquinolin-8-yl | O | 0 | 1 | H | H | H | CH$_2$CONH$_2$ | 232-234 |
| 72. | 5-chloroquinolin-8-yl | O | 0 | 2 | H | H | H | CH$_2$CONH$_2$ | 183-185 |
| 73. | 5-chloroquinolin-8-yl | O | 0 | 3 | H | H | H | CH$_2$CONH$_2$ | 184-186 |
| 74. | phenyl | O | 1 | 0 | H | H | CH$_3$ | CH$_2$CONH$_2$ | 90-92 |
| 75. | 4-CF$_3$-phenyl | O | 0 | 2 | (CH$_2$)$_2$ | H | | CH$_2$CONH$_2$ | 115-117 |
| 76. | 4-Cl-phenyl | SO$_2$ | 0 | 2 | (CH$_2$)$_2$ | H | | CH$_2$CONH$_2$ | 164-166 |
| 77. | 4-Cl-phenyl | SO$_2$ | 0 | 2 | (CH$_2$)$_2$ | H | | CH$_2$CONHCH$_3$ | 168-170 |
| 78. | 3-CF$_3$-phenyl | SO$_2$ | 0 | 2 | (CH$_2$)$_2$ | H | | CH$_2$CONH$_2$ | 148-150 |
| 79. | 3-CF$_3$-phenyl | SO$_2$ | 0 | 2 | (CH$_2$)$_2$ | H | | CH$_2$CONHCH$_3$ | 163-165 |
| 80. | naphthalen-1-yl | O | 0 | 1 | (CH$_2$)$_2$ | H | | CH$_2$CONHCH$_3$ | 111-113 |
| 81. | naphthalen-1-yl | O | 1 | 1 | CH$_2$ | | | CH$_2$CONH$_2$ | 176-178 |
| 82. | naphthalen-1-yl | O | 1 | 1 | CH$_2$ | | H | CH$_2$CONHCH$_3$ | 112-114 |
| 83. | naphthalen-1-yl | O | 1 | 1 | (CH$_2$)$_2$ | H | | CH$_2$CONH$_2$ | 161-163 |
| 84. | naphthalen-1-yl | O | 1 | 1 | (CH$_2$)$_2$ | H | | CH$_2$CONHCH$_3$ | 99-101 |
| 85. | 4-(4-F-phenyl)phenyl | O | 0 | 2 | (CH$_2$)$_2$ | H | | CH$_2$CONHCH$_3$ | 117-119 |
| 86. | 4-(4-Cl-phenyl)phenyl | O | 0 | 2 | (CH$_2$)$_2$ | H | | CH$_2$CONHCH$_3$ | 134-136 |
| 87. | 4-(4-CH$_3$-phenyl)phenyl | O | 0 | 2 | (CH$_2$)$_2$ | H | | CH$_2$CONHCH$_3$ | 121-123 |
| 88. | 4-(4-n-butyl-phenyl)phenyl | O | 0 | 2 | (CH$_2$)$_2$ | H | | CH$_2$CONHCH$_3$ | 105-107 |
| 89. | 4-(4-CF$_3$-phenyl)phenyl | O | 0 | 2 | (CH$_2$)$_2$ | H | | CH$_2$CONHCH$_3$ | 141-143 |
| 90. | 4-(4-CH$_3$O-phenyl)phenyl | O | 0 | 2 | (CH$_2$)$_2$ | H | | CH$_2$CONHCH$_3$ | 152-154 |
| 91. | 4-(4-C$_2$H$_5$O-phenyl)phenyl | O | 0 | 2 | (CH$_2$)$_2$ | H | | CH$_2$CONHCH$_3$ | 145-147 |
| 92. | 4-(4-CF$_3$O-phenyl)phenyl | O | 0 | 2 | (CH$_2$)$_2$ | H | | CH$_2$CONHCH$_3$ | 131-133 |
| 93. | 4-(3-F,4-CH$_3$O-phenyl)phenyl | O | 0 | 2 | (CH$_2$)$_2$ | H | | CH$_2$CONHCH$_3$ | (417) |
| 94. | 4-(3-Cl,4-F-phenyl)phenyl | O | 0 | 2 | (CH$_2$)$_2$ | H | | CH$_2$CONHCH$_3$ | 124-126 |
| 95. | 4-(3,4-Cl$_2$-phenyl)phenyl | O | 0 | 2 | (CH$_2$)$_2$ | H | | CH$_2$CONHCH$_3$ | (438) |
| 96. | 3-(4-F-phenyl)phenyl | O | 0 | 2 | (CH$_2$)$_2$ | H | | CH$_2$CONHCH$_3$ | (387) |
| 97. | 3-(4-Cl-phenyl)phenyl | O | 0 | 2 | (CH$_2$)$_2$ | H | | CH$_2$CONHCH$_3$ | (403) |
| 98. | 3-(4-CH$_3$-phenyl)phenyl | O | 0 | 2 | (CH$_2$)$_2$ | H | | CH$_2$CONHCH$_3$ | (383) |
| 99. | 3-(4-n-butylphenyl)phenyl | O | 0 | 2 | (CH$_2$)$_2$ | H | | CH$_2$CONHCH$_3$ | (425) |
| 100. | 3-(4-CF$_3$-phenyl)phenyl | O | 0 | 2 | (CH$_2$)$_2$ | H | | CH$_2$CONHCH$_3$ | (437) |
| 101. | 3-(4-CH$_3$O-phenyl)phenyl | O | 0 | 2 | (CH$_2$)$_2$ | H | | CH$_2$CONHCH$_3$ | (399) |
| 102. | 3-(4-C$_2$H$_5$O-phenyl)phenyl | O | 0 | 2 | (CH$_2$)$_2$ | H | | CH$_2$CONHCH$_3$ | (413) |
| 103. | 3-(4-CF$_3$O-phenyl)phenyl | O | 0 | 2 | (CH$_2$)$_2$ | H | | CH$_2$CONHCH$_3$ | (453) |
| 104. | 3-(3-F,4-CH$_3$O-phenyl)phenyl | O | 0 | 2 | (CH$_2$)$_2$ | H | | CH$_2$CONHCH$_3$ | (417) |
| 105. | 3-(3-Cl,4-F-phenyl)-phenyl | O | 0 | 2 | (CH$_2$)$_2$ | H | | CH$_2$CONHCH$_3$ | (421) |
| 106. | 3-(3,4-Cl$_2$-phenyl)phenyl | O | 0 | 2 | (CH$_2$)$_2$ | H | | CH$_2$CONHCH$_3$ | (438) |
| 107. | 3-(2,4-Cl$_2$-phenyl)phenyl | O | 0 | 2 | (CH$_2$)$_2$ | H | | CH$_2$CONHCH$_3$ | (438) |
| 108. | naphthalen-1-yl | O | 0 | 2 | (CH$_2$)$_2$ | H | | CH$_2$CONH$_2$ | 137-138 |
| 109. | naphthalen-1-yl | O | 0 | 2 | (CH$_2$)$_2$ | H | | CH$_2$CONHCH$_3$ | 121-122 |
| 110. | naphthalen-2-yl | O | 0 | 2 | (CH$_2$)$_2$ | H | | CH$_2$CONH$_2$ | 118-120 |
| 111. | quinolin-8-yl | O | 0 | 2 | (CH$_2$)$_2$ | H | | CH$_2$CONH$_2$ | (330) |
| 112. | phenyl | O | 1 | 2 | (CH$_2$)$_2$ | H | | CH$_2$CONH$_2$ | 123-125 |
| 113. | 4-Cl-phenyl | O | 1 | 2 | (CH$_2$)$_2$ | H | | CH$_2$CONH$_2$ | 152-154 |
| 114. | 4-Cl-phenyl | O | 1 | 2 | (CH$_2$)$_2$ | H | | CH$_2$CONHCH$_3$ | 166-168 |
| 115. | 4-Cl-phenyl | S | 1 | 2 | (CH$_2$)$_2$ | H | | CH$_2$CONHCH$_3$ | 130-132 |
| 116. | 4-Cl-phenyl | SO$_2$ | 1 | 2 | (CH$_2$)$_2$ | H | | CH$_2$CONHCH$_3$ | 131-133 |
| 117. | 3-Cl-phenyl | O | 1 | 2 | (CH$_2$)$_2$ | H | | CH$_2$CONH$_2$ | 131-133 |

TABLE-continued (I)

Y—X—(CH2)m—C(R1)(R3)—(CH2)n—N(R2)—C(=O)—O—R4

| Cpd | Y | X | m | n | R1 | R2 | R3 | R4 | m.p. °C. (or M + H) |
|---|---|---|---|---|---|---|---|---|---|
| 118. | 3-Cl-phenyl | S | 1 | 2 | (CH$_2$)$_2$ | H | | CH$_2$CONHCH$_3$ | 94-96 |
| 119. | 3-Cl-phenyl | SO$_2$ | 1 | 2 | (CH$_2$)$_2$ | H | | CH$_2$CONHCH$_3$ | 100-102 |
| 120. | 4-Br-phenyl | O | 1 | 2 | (CH$_2$)$_2$ | H | | CH$_2$CONHCH$_3$ | 163-165 |
| 121. | 4-CH$_3$O-phenyl | O | 1 | 2 | (CH$_2$)$_2$ | H | | CH$_2$CONH$_2$ | 128-130 |
| 122. | 3-CH$_3$O-phenyl | O | 1 | 2 | (CH$_2$)$_2$ | H | | CH$_2$CONH$_2$ | 119-121 |
| 123. | 4-n-propyloxyphenyl | O | 1 | 2 | (CH$_2$)$_2$ | H | | CH$_2$CONH$_2$ | 141-143 |
| 124. | 4-CF$_3$-phenyl | O | 1 | 2 | (CH$_2$)$_2$ | H | | CH$_2$CONH$_2$ | 134-136 |
| 125. | 4-CF$_3$-phenyl | S | 1 | 2 | (CH$_2$)$_2$ | H | | CH$_2$CONHCH$_3$ | 129-131 |
| 126. | 4-CF$_3$-phenyl | SO$_2$ | 1 | 2 | (CH$_2$)$_2$ | H | | CH$_2$CONHCH$_3$ | 103-105 |
| 127. | 3-CF$_3$-phenyl | O | 1 | 2 | (CH$_2$)$_2$ | H | | CH$_2$CONH$_2$ | 120-121 |
| 128. | 3-CF$_3$-phenyl | S | 1 | 2 | (CH$_2$)$_2$ | H | | CH$_2$CONHCH$_3$ | 167-169 |
| 129. | 3-CF$_3$-phenyl | SO$_2$ | 1 | 2 | (CH$_2$)$_2$ | H | | CH$_2$CONHCH$_3$ | 141-143 |
| 130. | 4-CF$_3$O-phenyl | O | 1 | 2 | (CH$_2$)$_2$ | H | | CH$_2$CONH$_2$ | 118-120 |
| 131. | 3-CF$_3$O-phenyl | O | 1 | 2 | (CH$_2$)$_2$ | H | | CH$_2$CONH$_2$ | 132-134 |
| 132. | 4-isopropylphenyl | O | 1 | 2 | (CH$_2$)$_2$ | H | | CH$_2$CONH$_2$ | 113-115 |
| 133. | 3-isopropylphenyl | O | 1 | 2 | (CH$_2$)$_2$ | H | | CH$_2$CONH$_2$ | 119-121 |
| 134. | 2,3-Cl$_2$-phenyl | O | 1 | 2 | (CH$_2$)$_2$ | H | | CH$_2$CONHCH$_3$ | 160-162 |
| 135. | 2,4-Cl$_2$-phenyl | O | 1 | 2 | (CH$_2$)$_2$ | H | | CH$_2$CONHCH$_3$ | 144-146 |
| 136. | 3,4-Cl$_2$-phenyl | O | 1 | 2 | (CH$_2$)$_2$ | H | | CH$_2$CONH$_2$ | 113-115 |
| 137. | naphthalen-1-yl | O | 1 | 2 | (CH$_2$)$_2$ | H | | CH$_2$CONH$_2$ | 135-136 |
| 138. | naphthalen-1-yl | O | 1 | 2 | (CH$_2$)$_2$ | H | | CH$_2$CONHCH$_3$ | 151-152 |
| 139. | naphthalen-1-yl | O | 1 | 1 | (CH$_2$)$_3$ | H | | CH$_2$CONH$_2$ | 149-151 |
| 140. | naphthalen-1-yl | O | 1 | 1 | (CH$_2$)$_3$ | H | | CH$_2$CONHCH$_3$ | (357) |
| 141. | naphthalen-1-yl | S | 1 | 2 | (CH$_2$)$_2$ | H | | CH$_2$CONHCH$_3$ | 127-129 |
| 142. | naphthalen-1-yl | SO$_2$ | 1 | 2 | (CH$_2$)$_2$ | H | | CH$_2$CONHCH$_3$ | 154-156 |
| 143. | naphthalen-2-yl | O | 1 | 2 | (CH$_2$)$_2$ | H | | CH$_2$CONH$_2$ | 142-144 |
| 144. | naphthalen-2-yl | S | 1 | 2 | (CH$_2$)$_2$ | H | | CH$_2$CONHCH$_3$ | 111-113 |
| 145. | naphthalen-2-yl | SO$_2$ | 1 | 2 | (CH$_2$)$_2$ | H | | CH$_2$CONHCH$_3$ | 105-107 |
| 146. | 4-chloronaphthalen-1-yl | O | 1 | 2 | (CH$_2$)$_2$ | H | | CH$_2$CONH$_2$ | 166-168 |
| 147. | 4-chloronaphthalen-1-yl | O | 1 | 2 | (CH$_2$)$_2$ | H | | CH$_2$CONHCH$_3$ | 163-165 |
| 148. | quinolin-7-yl | O | 1 | 2 | (CH$_2$)$_2$ | H | | CH$_2$CONH$_2$ | 137-139 |
| 149. | isoquinolin-7-yl | O | 1 | 2 | (CH$_2$)$_2$ | H | | CH$_2$CONH$_2$ | 162-164 |
| 150. | 4-(4-F-phenyl)phenyl | O | 1 | 2 | (CH$_2$)$_2$ | H | | CH$_2$CONHCH$_3$ | 150-152 |
| 151. | 4-(4-Cl-phenyl)phenyl | O | 1 | 2 | (CH$_2$)$_2$ | H | | CH$_2$CONHCH$_3$ | 167-169 |
| 152. | 4-(4-CH$_3$-phenyl)phenyl | O | 1 | 2 | (CH$_2$)$_2$ | H | | CH$_2$CONHCH$_3$ | 164-166 |
| 153. | 4-(4-n-butyl-phenyl)-phenyl | O | 1 | 2 | (CH$_2$)$_2$ | H | | CH$_2$CONHCH$_3$ | 171-173 |
| 154. | 4-(4-CF$_3$-phenyl)phenyl | O | 1 | 2 | (CH$_2$)$_2$ | H | | CH$_2$CONHCH$_3$ | 197-199 |
| 155. | 4-(4-CH$_3$O-phenyl)phenyl | O | 1 | 2 | (CH$_2$)$_2$ | H | | CH$_2$CONHCH$_3$ | 172-174 |
| 156. | 4-(4-C$_2$H$_5$O-phenyl)phenyl | O | 1 | 2 | (CH$_2$)$_2$ | H | | CH$_2$CONHCH$_3$ | 173-175 |
| 157. | 4-(4-CF$_3$O-phenyl)phenyl | O | 1 | 2 | (CH$_2$)$_2$ | H | | CH$_2$CONHCH$_3$ | 152-154 |
| 158. | 4-(3-F,4-CH$_3$O-phenyl)-phenyl | O | 1 | 2 | (CH$_2$)$_2$ | H | | CH$_2$CONHCH$_3$ | 156-158 |
| 159. | 4-(3-Cl, 4-F-phenyl)-phenyl | O | 1 | 2 | (CH$_2$)$_2$ | H | | CH$_2$CONHCH$_3$ | 132-134 |
| 160. | 4-(3,4-Cl$_2$-phenyl)phenyl | O | 1 | 2 | (CH$_2$)$_2$ | H | | CH$_2$CONHCH$_3$ | 163-165 |
| 161. | 4-(2,4-Cl$_2$-phenyl)phenyl | O | 1 | 2 | (CH$_2$)$_2$ | H | | CH$_2$CONHCH$_3$ | 177-179 |
| 162. | pyrimidin-2-yl | S | 1 | 2 | (CH$_2$)$_2$ | H | | CH$_2$CONHCH$_3$ | 109-111 |
| 163. | 5-phenylthiazol-2-yl | S | 1 | 2 | (CH$_2$)$_2$ | H | | CH$_2$CONHCH$_3$ | (406) |
| 164. | benzoxazol-2-yl | S | 1 | 2 | (CH$_2$)$_2$ | H | | CH$_2$CONHCH$_3$ | (364) |
| 165. | phenyl | O | 2 | 2 | (CH$_2$)$_2$ | H | | CH$_2$CONH$_2$ | 136-138 |
| 166. | 4-Cl-phenyl | O | 2 | 2 | (CH$_2$)$_2$ | H | | CH$_2$CONH$_2$ | 115-117 |
| 167. | 3-Cl-phenyl | O | 2 | 2 | (CH$_2$)$_2$ | H | | CH$_2$CONH$_2$ | 91-93 |
| 168. | 4-Br-phenyl | O | 2 | 2 | (CH$_2$)$_2$ | H | | CH$_2$CONHCH$_3$ | 101-103 |
| 169. | 4-CH$_3$O-phenyl | O | 2 | 2 | (CH$_2$)$_2$ | H | | CH$_2$CONH$_2$ | 108-110 |
| 170. | 3-CH$_3$O-phenyl | O | 2 | 2 | (CH$_2$)$_2$ | H | | CH$_2$CONH$_2$ | (337) |
| 171. | 4-n-propyloxy-phenyl | O | 2 | 2 | (CH$_2$)$_2$ | H | | CH$_2$CONH$_2$ | 121-123 |
| 172. | 4-CF$_3$-phenyl | O | 2 | 2 | (CH$_2$)$_2$ | H | | CH$_2$CONH$_2$ | 112-114 |
| 173. | 3-CF$_3$-phenyl | O | 2 | 2 | (CH$_2$)$_2$ | H | | CH$_2$CONH$_2$ | 94-96 |
| 174. | 4-CF$_3$O-phenyl | O | 2 | 2 | (CH$_2$)$_2$ | H | | CH$_2$CONH$_2$ | 79-81 |
| 175. | 3-CF$_3$O-phenyl | O | 2 | 2 | (CH$_2$)$_2$ | H | | CH$_2$CONH$_2$ | (391) |
| 176. | 4-isopropylphenyl | O | 2 | 2 | (CH$_2$)$_2$ | H | | CH$_2$CONH$_2$ | 75-77 |
| 177. | 3-isopropylphenyl | O | 2 | 2 | (CH$_2$)$_2$ | H | | CH$_2$CONH$_2$ | (349) |
| 178. | 3,4-Cl$_2$-phenyl | O | 2 | 2 | (CH$_2$)$_2$ | H | | CH$_2$CONH$_2$ | 103-105 |
| 179. | naphthalen-1-yl | O | 2 | 2 | (CH$_2$)$_2$ | H | | CH$_2$CONH$_2$ | 134-135 |
| 180. | naphthalen-1-yl | O | 2 | 2 | (CH$_2$)$_2$ | H | | CH$_2$CONHCH$_3$ | 108-109 |
| 181. | naphthalen-2-yl | O | 2 | 2 | (CH$_2$)$_2$ | H | | CH$_2$CONH$_2$ | (357) |
| 182. | quinolin-7-yl | O | 2 | 2 | (CH$_2$)$_2$ | H | | CH$_2$CONH$_2$ | 164-166 |
| 183. | isoquinolin-7-yl | O | 2 | 2 | (CH$_2$)$_2$ | H | | CH$_2$CONH$_2$ | 179-181 |
| 184. | 4-phenylphenyl | O | 2 | 2 | (CH$_2$)$_2$ | H | | CH$_2$CONHCH$_3$ | 124-126 |

TABLE-continued (I)

$$Y-X-(CH_2)m-\underset{R_1}{\overset{R_3}{C}}-(CH_2)n-\underset{R_2}{N}-\overset{O}{\underset{}{C}}-O-R_4$$

| Cpd | Y | X | m | n | $R_1$ $R_2$ | $R_3$ | $R_4$ | m.p. ° C. (or M + H) |
|---|---|---|---|---|---|---|---|---|
| 185. | 4-(4-F-phenyl)phenyl | O | 2 | 2 | $(CH_2)_2$ | H | $CH_2CONHCH_3$ | 120-122 |
| 186. | 4-(4-Cl-phenyl)phenyl | O | 2 | 2 | $(CH_2)_2$ | H | $CH_2CONHCH_3$ | 104-106 |
| 187. | 4-(4-CF$_3$-phenyl)phenyl | O | 2 | 2 | $(CH_2)_2$ | H | $CH_2CONHCH_3$ | 137-139 |
| 188. | 4-(3-CF$_3$-phenyl)phenyl | O | 2 | 2 | $(CH_2)_2$ | H | $CH_2CONHCH_3$ | 98-100 |
| 189. | 4-(4-CH$_3$O-phenyl)phenyl | O | 2 | 2 | $(CH_2)_2$ | H | $CH_2CONHCH_3$ | 141-143 |
| 190. | 4-(4-CF$_3$O-phenyl)phenyl | O | 2 | 2 | $(CH_2)_2$ | H | $CH_2CONHCH_3$ | 116-118 |
| 191. | 4-(4-iso-propyl-phenyl)phenyl | O | 2 | 2 | $(CH_2)_2$ | H | $CH_2CONHCH_3$ | 121-123 |
| 192. | 4-(2,4-Cl$_2$-phenyl)phenyl | O | 2 | 2 | $(CH_2)_2$ | H | $CH_2CONHCH_3$ | 112-114 |

The compounds of the invention were subjected to pharmacological tests permitting determination of their inhibitory effect on the enzyme FAAH (Fatty Acid Amide Hydrolase).

The inhibitory activity was demonstrated in a radioenzymatic assay based on measuring the product of hydrolysis (ethanolamine [1-$^3$H]) of anandamide [ethanolamine 1-$^3$H] by FAAH (*Life Sciences* (1995), 56, 1999-2005 and *Journal of Pharmacology and Experimental Therapeutics* (1997), 283, 729-734). Accordingly, mouse brains (minus the cerebellum) are removed and stored at −80° C. Membrane homogenates are prepared at the time of use by homogenizing the tissues in a Polytron in a 10 mM Tris-HCl buffer (pH 8.0) containing 150 mM NaCl and 1 mM EDTA. The enzyme reaction is subsequently conducted in 70 μl of buffer containing bovine serum albumin without fatty acids (1 mg/ml). In succession, the test compounds, at various concentrations, anandamide [ethanolamine 1-$^3$H] (specific activity: 15-20 Ci/mmol) diluted to 10 μM with cold anandamide, and the membrane preparation (400 μg of frozen tissue per assay) are added. After 15 minutes at 25° C. the enzyme reaction is terminated by adding 140 μl of chloroform/methanol (2:1). The mixture is stirred for 10 minutes and then centrifuged for 15 minutes at 3500 g. An aliquot (30 μl) of the aqueous phase containing the ethanolamine [1-$^3$H] is counted by liquid scintillation.

Under these conditions, the most active compounds of the invention exhibit $IC_{50}$ values (concentration inhibiting by 50% the control enzyme activity of FAAH) of between 0.001 and 1 μM. For example, compound 58 of the table exhibits an $IC_{50}$ of 0.47 μM.

It is therefore apparent that the compounds according to the invention have an inhibitory effect on the FAAH enzyme.

The in vivo activity of the compounds of the invention was evaluated in an analgesia test.

Accordingly, intraperitoneal (i.p.) administration of PBQ (phenylbenzoquinone, 2 mg/kg in a 0.9% sodium chloride solution containing 5% of ethanol) to male OF1 mice weighing 25 to 30 g causes abdominal stretches, on average 30 twists or contractions during the period from 5 to 15 minutes after injection. The test compounds are administered orally in suspension in Tween 80 at 0.5%, 60 minutes or 120 minutes before the administration of PBQ. Under these conditions the most potent compounds of the invention reduce by 35 to 70% the number of stretches induced by PBQ, within a dose range of between 1 and 30 mg/kg. For example, compound 58 of the table reduces by 51% the number of stretches induced by PBQ, at a dose of 1 mg/kg at 2 hours.

The enzyme FAAH (*Chemistry and Physics of Lipids*, (2000), 108, 107-121) catalyses the hydrolysis of endogenous derivatives of amides and of esters of various fatty acids such as N-arachidonylethanolamine (anandamide), N-palmitoylethanolamine, N-oleoyl-ethanolamine, oleamide or 2-arachidonoylglycerol. These derivatives exert various pharmacological activities by interacting, inter alia, with cannabinoid and vanilloid receptors.

The compounds of the invention block this degradation pathway and increase the tissue level of these endogenous substances. They can be used in this respect in the prevention and treatment of pathologies in which endogenous cannabinoids and/or any other substrates metabolized by the FAAH enzyme are involved.

Mention may be made, for example, of the following diseases and conditions: pain, especially acute or chronic pain of the neurogenic type: migraine, neuropathic pain, including forms associated with the herpes virus and with diabetes; acute or chronic pain associated with inflammatory diseases: arthritis, rheumatoid arthritis, osteoarthritis, spondylitis, gout, vasculitis, Crohn's disease, irritable bowel syndrome; acute or chronic peripheral pain;

dizziness, vomiting, nausea, especially those subsequent to chemotherapy;

eating disorders, especially anorexia and cachexia of various kinds;

neurological and psychiatric pathologies: shaking, dyskinesia, dystonia, spasticity, obsessive-compulsive behaviors, Tourette's syndrome, all forms of depression and anxiety of any kind and cause, mood disorders, psychoses; acute and chronic neurodegenerative diseases: Parkinson's disease, Alzheimer's disease, senile dementia, Huntington's chorea, lesions associated with cerebral ischemia and with cranial and medullary trauma;

epilepsy;

sleep disorders, including sleep apnea;

cardiovascular diseases, especially hypertension, cardiac arrhythmias, arteriosclerosis, heart attack, cardiac ischemias;

renal ischemia;

cancers: benign skin tumors, papillomas and brain tumors, prostate tumors, brain tumors (glioblastomas, medulloepitheliomas, medulloblastomas, neuroblastomas, tumors of embryonic origin, astrocytomas, astroblastomas, ependyomas, oligodendrogliomas, plexus tumor, neuroepitheliomas, epiphyseal tumor, ependymoblastomas, malignant meningiomas, sarcomatoses, malignant melanomas, schwannomas);

disorders of the immune system, especially autoimmune diseases: psoriasis, lupus erythematosis, diseases of the connective tissue or collagen diseases, Sjögrer's syndrome, ankylosing spondylarthritis, undifferentiated spondylarthritis, Behcet's disease, haemolytic autoimmune anaemias, multiple sclerosis, amyotrophic lateral sclerosis, amyloses, transplant rejection, diseases affecting the plasmocytic line;

allergic diseases: immediate or delayed hypersensitivity, allergic rhinitis or conjunctivitis, contact dermatitis;

parasitic, viral or bacterial infectious diseases: AIDS, meningitis; inflammatory diseases, especially diseases of the joints: arthritis, rheumatoid arthritis, osteoarthritis, spondylitis, gout, vasculitis, Crohn's disease, irritable bowel syndrome;

osteoporosis; ocular conditions: ocular hypertension, glaucoma;

pulmonary conditions: diseases of the respiratory tracts, bronchospasms, coughing, asthma, chronic bronchitis, chronic obstruction of the respiratory tracts, emphysema;

gastrointestinal diseases: irritable bowel syndrome, intestinal inflammatory disorders, ulcers, diarrhea;

urinary incontinence and bladder inflammation.

The use of compounds of formula (I) in base, salt, hydrate or pharmaceutically acceptable solvate form for preparing a medicinal product intended for treating the abovementioned pathologies forms an integral part of the invention.

The invention likewise provides medicinal products which comprise a compound of formula (I), or a salt or else a hydrate or a pharmaceutically acceptable solvate of the compound of formula (I). These medicinal products are employed in therapy, particularly in the treatment of the abovementioned pathologies.

In accordance with another of its aspects the present invention provides pharmaceutical compositions comprising as active principle at least one compound of formula (I). These pharmaceutical compositions include an effective dose of a compound according to the invention, or a salt or a hydrate or pharmaceutically acceptable solvate of the said compound, and optionally one or more pharmaceutically acceptable excipients.

Said excipients are selected, according to the pharmaceutical form and the desired mode of administration, from the customary excipients, which are known to the person skilled in the art.

In the pharmaceutical compositions of the present invention for oral, sublingual, subcutaneous, intramuscular, intravenous, topical, local, intrathecal, intranasal, transdermal, pulmonary, ocular or rectal administration the active principle of formula (I) above, or its salt, solvate or hydrate where appropriate, may be administered in single-dose administration form, in a mixture with conventional pharmaceutical excipients, to animals and to humans for the prophylaxis or treatment of the above disorders or diseases.

The unit-dose administration forms which are appropriate include oral forms such as tablets, soft or hard gelatin capsules, powders, granules, chewing gums and oral solutions or suspensions, forms for sublingual, buccal, intratracheal, intraocular and intranasal administration and for administration by inhalation, forms for subcutaneous, intramuscular or intravenous administration and forms for rectal or vaginal administration. For topical application the compounds according to the invention may be used in creams, ointments or lotions.

By way of example a single-dose administration form of a compound according to the invention in tablet form may comprise the following components:

| Compound according to the invention | 50.0 mg |
| Mannitol | 223.75 mg |
| Croscaramellose sodium | 6.0 mg |
| Maize starch | 15.0 mg |
| Hydroxypropyl-methylcellulose | 2.25 mg |
| Magnesium stearate | 3.0 mg |

The said single-dose forms contain a dose permitting daily administration of from 0.01 to 20 mg of active principle per kg of bodyweight, depending on the pharmaceutical form.

There may be particular cases in which higher or lower dosages are appropriate; such dosages also belong to the invention. In accordance with common practice the dosage appropriate to each patient is determined by the doctor according to the method of administration, the weight and the response of the said patient.

According to another of its aspects the invention also provides a method of treating the pathologies indicated above, which comprises administering an effective dose of a compound according to the invention, one of its pharmaceutically acceptable salts, or a solvate or a hydrate of the said compound.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound of the formula (I):

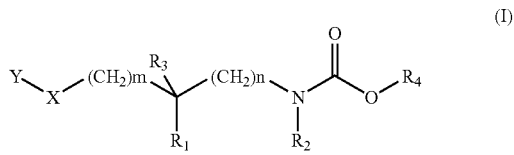

wherein m is 0, 1, 2 or 3;

n is 0, 1, 2 or 3;

X is oxygen, sulfur, SO or $SO_2$;

$R_1$ and $R_2$ are independently of one another hydrogen or $C_{1-3}$ alkyl; or $R_1$ and $R_2$ together form a group —$(CH_2)_p$—, where p represents an integer ranging from 1 to 5 such that n+p is an integer ranging from 2 to 5;

$R_3$ is hydrogen, fluorine, hydroxyl or methyl;

$R_4$ is a group of formula $CHR_5CONHR_6$; wherein $R_5$ is hydrogen or $C_{1-6}$ alkyl; and $R_6$ is hydrogen, $C_{1-6}$ alkyl, $C_{3-7}$ cycloalkyl or $C_{3-7}$ cycloalkyl-$C_{1-6}$ alkylene; and Y is selected from phenyl, pyridinyl, pyridazinyl, pyrimidinyl, pyrazinyl, triazinyl, thiazolyl, naphthyl, quinolinyl, isoquinolinyl, phthalazinyl, quinazolinyl, quinoxalinyl, naphthyridinyl, cinnolinyl, benzofuranyl, dihydrobenzofuranyl, benzothienyl, dihydrobenzothienyl, indolyl, isoindolyl, indolinyl, benzimidazolyl, benzoxazolyl, benzisoxazolyl, benzothiazolyl, benzisothiazolyl, benzotriazolyl, benzoxadiazolyl and benzothiadiazolyl; said Y is optionally substituted by one or more substituents $Y_2$, which are identical to or different from one another, or by $Y_3$; wherein $Y_2$ is halogen, cyano, nitro, $C_{1-8}$ alkyl, $C_{1-8}$ alkoxy, $C_{1-8}$ thioalkyl, $C_{1-8}$ fluoroalkyl, $C_{1-8}$ fluoroalkoxy, $C_{1-8}$ fluorothioalkyl, $C_{3-7}$ cycloalkyl, $C_{3-7}$ cycloalkyloxy, $C_{3-7}$ cycloalkyl-$C_{1-8}$ alkylene, $C_{3-7}$ cycloalkyl-$C_{1-8}$ alkyloxy, hydroxyl, $NR_7R_8$, $NHCOR_7$, $NHSO_2R_7$, $COR_7$, $CO_2R_7$, $CONR_7R_8$, $SO_2R_7$, $SO_2NR_7R_8$, —O—($C_{1-3}$ alkylene)-O—, phenyloxy, phenylthio, phenyl-$C_1$-$C_8$ alkylene, phenyl-$C_1$-$C_8$ alkyloxy or phenyl-$C_1$-$C_8$ alkylthio group;

$Y_3$ is selected from phenyl, pyridinyl, pyrimidinyl, pyrazinyl or pyridazinyl; said $Y_3$ is optionally substituted by one or more substituents selected from $Y_2$ which are identical to or different from one another;

$R_7$ and $R_8$ are independently of one another hydrogen or $C_{1-6}$ alkyl; or $R_7$ and $R_8$ with the nitrogen atom carrying them form an azetidine, pyrrolidine, piperidine, morpholine, thiomorpholine, azepine or piperazine ring optionally substituted by $C_{1-3}$ alkyl or benzyl;

with the proviso that, when $R_1$ and $R_2$ are independently of one another hydrogen or $C_{1-3}$ alkyl, m+n>1; or a salt thereof.

2. The compound of formula (I) according to claim 1, wherein

Y is selected from phenyl, pyridinyl, pyrimidinyl, thiazolyl, naphthyl, quinolinyl, isoquinolinyl and benzoxazolyl; said Y is optionally substituted by one or more substituents $Y_2$, which are identical to or different from one another, or by $Y_3$; wherein $Y_2$ is halogen, cyano, $C_{1-8}$ alkyl, $C_{1-8}$ alkoxy, $C_{1-8}$ fluoroalkyl, $C_{1-8}$ fluoroalkoxy, phenyloxy or phenyl-$C_1$-$C_8$ alkylene; and $Y_3$ is phenyl optionally substituted by one or more substituents selected from $Y_2$ which are identical to or different from one another; or a salt thereof.

3. The compound of formula (I) according to claim 1, wherein

Y is selected from phenyl or naphthyl; said Y is optionally substituted by one or more substituents $Y_2$, which are identical to or different from one another, or by $Y_3$; wherein $Y_2$ is halogen, cyano, $C_{1-8}$ alkyl, $C_{1-8}$ alkoxy, $C_{1-8}$ fluoroalkyl, $C_{1-8}$ fluoroalkoxy, phenyloxy or phenyl-$C_1$-$C_8$ alkylene; and $Y_3$ is phenyl optionally substituted by one or more substituents selected from $Y_2$ which are identical to or different from one another; or a salt thereof.

4. The compound of formula (I) according to claim 1, wherein m is 0, 1, 2 or 3;

n is 0, 1, 2 or 3;

$R_1$ and $R_2$ are independently of one another hydrogen or $C_{1-3}$ alkyl; or $R_1$ and $R_2$ together form a group —$(CH_2)_p$—, where p is an integer ranging from 1 to 5 such that n+p is an integer ranging from 2 to 5; or a salt thereof.

5. The compound of formula (I) according to claim 1, wherein m is 0, 1, 2 or 3;

n is 0, 1, 2 or 3;

$R_1$ and $R_2$ together form a group —$(CH_2)_p$—, where p is an integer ranging from 1 to 4 such that n+p is equal to 4; or a salt thereof.

6. The compound of formula (I) according to claim 1, wherein X is oxygen; or a salt thereof.

7. The compound of formula (I) according to claim 1, wherein $R_3$ is hydrogen; or a salt thereof.

8. A process for preparing a compound of formula (I) according to claim 1, comprising the step of reacting a compound of formula (IV)

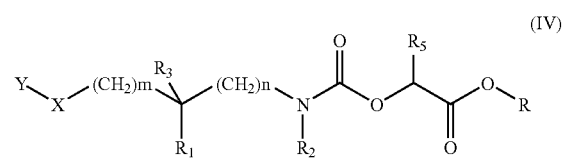

wherein Y, X, $R_1$, $R_2$, $R_3$, $R_5$, m and n are as defined according to claim 1 and R is methyl or ethyl, with an amine of formula $R_6NH_2$ where $R_6$ is as defined in formula (I) according to claim 1.

9. A pharmaceutical composition comprising at least one compound of formula (I) according to claim 1, or a pharmaceutically acceptable salt thereof, in combination with one or more pharmaceutically acceptable excipients.

\* \* \* \* \*